(12) United States Patent
Drew

(10) Patent No.: US 7,765,088 B2
(45) Date of Patent: Jul. 27, 2010

(54) PEAK DATA RETENTION OF SIGNAL DATA IN AN IMPLANTABLE MEDICAL DEVICE

(75) Inventor: Touby A. Drew, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 228 days.

(21) Appl. No.: 12/037,694

(22) Filed: Feb. 26, 2008

(65) Prior Publication Data
US 2008/0235469 A1 Sep. 25, 2008

Related U.S. Application Data

(63) Continuation of application No. 11/380,586, filed on Apr. 27, 2006, now Pat. No. 7,359,837.

(51) Int. Cl.
*G06F 12/00* (2006.01)
*G06F 17/00* (2006.01)

(52) U.S. Cl. .................. 702/189; 702/80; 702/187; 600/523; 711/100

(58) Field of Classification Search .............. 702/189, 702/80, 178, 187
See application file for complete search history.

(56) References Cited

U.S. PATENT DOCUMENTS

| | | | |
|---|---|---|---|
| 3,958,563 A | 5/1976 | Fernandez | |
| 4,374,382 A | 2/1983 | Markowitz | |
| 4,485,813 A | 12/1984 | Anderson | |
| 4,556,063 A | 12/1985 | Thompson | |
| 4,567,892 A | 2/1986 | Plicchi | |
| 4,583,553 A | 4/1986 | Shah | |
| 4,596,251 A | 6/1986 | Plicchi | |
| 4,649,930 A | 3/1987 | Groch | |
| 4,903,701 A | 2/1990 | Moore | |
| 4,920,489 A * | 4/1990 | Hubelbank et al. .......... 600/519 |
| 4,964,410 A | 10/1990 | Leahey | |

(Continued)

FOREIGN PATENT DOCUMENTS

WO 2004023983 3/2004

(Continued)

OTHER PUBLICATIONS

International Search Report and Written Opinion for PCT/US2007/006431 mailed Aug. 16, 2007.

*Primary Examiner*—Hal D Wachsman
(74) *Attorney, Agent, or Firm*—Banner & Witcoff, Ltd.

(57) ABSTRACT

Storing data records associated with an extreme value are disclosed. Signal data is stored in a first buffer of a set of buffers. If a local extreme value for the first buffer exceeds a global extreme value, signal data is stored in a second buffer of the set of buffers. This process is repeated, wrapping around and overwriting buffers until the signal data in a current buffer does not have a local extreme value that exceeds the global extreme value. When this happens, signal data may be stored in a subsequent buffer and if a local extreme value of the subsequent buffer does not exceed the global extreme value, further signal data may be stored in the subsequent buffer in a circular manner until either an instantaneous extreme value exceeds the global extreme value or the recording period ends. In an embodiment, the extreme value may be a peak value.

17 Claims, 27 Drawing Sheets

U.S. PATENT DOCUMENTS

| | | | |
|---|---|---|---|
| 5,007,431 A | 4/1991 | Donehoo, III | |
| 5,052,388 A | 10/1991 | Sivula | |
| 5,127,404 A | 7/1992 | Wyborny | |
| 5,168,759 A | 12/1992 | Bowman | |
| 5,285,792 A | 2/1994 | Sjoquist | |
| 5,312,446 A | 5/1994 | Holschbach | |
| 5,336,244 A | 8/1994 | Weijand | |
| 5,354,318 A | 10/1994 | Taepke | |
| 5,409,009 A | 4/1995 | Olsen | |
| 5,431,691 A | 7/1995 | Snell | |
| 5,518,001 A | 5/1996 | Snell | |
| 5,554,177 A | 9/1996 | Kieval | |
| 5,752,976 A | 5/1998 | Duffin | |
| 5,782,891 A | 7/1998 | Hassler | |
| 5,908,392 A * | 6/1999 | Wilson et al. | 600/509 |
| 5,944,745 A | 8/1999 | Rueter | |
| 5,987,352 A | 11/1999 | Klein | |
| 5,995,868 A | 11/1999 | Dorfmeister | |
| 6,016,449 A | 1/2000 | Eischell | |
| 6,067,473 A | 5/2000 | Greeninger | |
| 6,128,538 A | 10/2000 | Fischell | |
| 6,200,265 B1 | 3/2001 | Walsh | |
| 6,227,203 B1 | 5/2001 | Rise | |
| 6,360,122 B1 | 3/2002 | Fischell | |
| 6,427,086 B1 | 7/2002 | Fischell | |
| 6,496,715 B1 | 12/2002 | Lee | |
| 6,505,067 B1 | 1/2003 | Lee | |
| 6,512,940 B1 | 1/2003 | Brabec | |
| 6,522,915 B1 | 2/2003 | Ceballos | |
| 6,549,804 B1 | 4/2003 | Osorio | |
| 6,599,242 B1 | 7/2003 | Splett | |
| 6,664,729 B2 | 12/2003 | Elledge | |
| 7,359,837 B2 | 4/2008 | Drew | |
| 2004/0138536 A1 | 7/2004 | Frei | |
| 2004/0230105 A1 | 11/2004 | Geva | |
| 2005/0081847 A1 | 4/2005 | Lee | |
| 2005/0113647 A1 | 5/2005 | Lee | |
| 2005/0203366 A1 | 9/2005 | Donoghue | |
| 2006/0195039 A1 * | 8/2006 | Drew et al. | 600/523 |

FOREIGN PATENT DOCUMENTS

WO        2004084722        10/2004

* cited by examiner

PEAK DATA RETENTION OF SIGNAL DATA IN AN IMPLANTABLE MEDICAL DEVICE

CROSS REFERENCE TO RELATED APPLICATIONS

This application is a continuation of application Ser. No. 11/380,586, filed Apr. 27, 2006, now U.S. Pat. No. 7,359,837, which is incorporated herein by reference in its entirety.

FIELD OF THE INVENTION

The invention relates to techniques for selecting, storing and reporting data associated with physiologic signals that may be further associated with a neurological event.

BACKGROUND OF THE INVENTION

Nervous system disorders affect millions of people, causing death and a degradation of life. Nervous system disorders include disorders of the central nervous system, peripheral nervous system, and mental health and psychiatric disorders. Such disorders include, for example without limitation, epilepsy, Parkinson's disease, essential tremor, dystonia, headache, and multiple sclerosis (MS). Additionally, as used herein, nervous system disorders include mental health disorders and psychiatric disorders which affect millions of individuals and include, but are not limited to, anxiety (such as general anxiety disorder, panic disorder, phobias, post traumatic stress disorder (PTSD), and obsessive compulsive disorder (OCD)), mood disorders (such as major depression, bipolar depression, and dysthymic disorder), sleep disorders (narcolepsy), obesity, and anorexia.

As an example, epilepsy is the most prevalent serious neurological disease across all ages. Epilepsy is a group of neurological conditions in which a person has or is predisposed to recurrent seizures. A seizure is a clinical manifestation resulting from excessive, hypersynchronous, abnormal electrical or neuronal activity in the brain. (A neurological event is an activity that is indicative of a nervous system disorder. A seizure is a type of a neurological event.) This electrical excitability of the brain may be likened to an intermittent electrical overload that manifests with sudden, recurrent, and transient changes of mental function, sensations, perceptions, and/or involuntary body movement. Because seizures are often unpredictable and the effect of a seizure varies, epilepsy affects a person's employability, psychosocial life, and ability to operate vehicles or power equipment. It is a disorder that occurs in all age groups, socioeconomic classes, cultures, and countries. In developed countries, the age-adjusted incidence of recurrent unprovoked seizures ranges from 24/100,000 to 53/100,000 person-years and may be even higher in developing countries. In developed countries, age specific incidence is highest during the first few months of life and again after age 70. The age-adjusted prevalence of epilepsy is 5 to 8 per 1,000 (0.5% to 0.8%) in countries where statistics are available. In the United States alone, epilepsy and seizures affect 2.3 million Americans, with approximately 181,000 new cases occurring each year. It is estimated that 10% of Americans will experience a seizure in their lifetimes, and 3% will develop epilepsy by age 75.

There are various approaches in treating nervous system disorders. Treatment therapies can include any number of possible modalities alone or in combination including, for example, electrical stimulation, magnetic stimulation, drug infusion, and/or brain temperature control. Each of these treatment modalities can be operated using closed-loop feedback control. Such closed-loop feedback control techniques receive from a monitoring element a neurological signal that carries information about a symptom or a condition or a nervous system disorder. Such a neurological signal can include, for example, electrical signals (such as EEG, ECoG, and/or EKG), chemical signals, other biological signals (such as change in quantity of neurotransmitters), temperature signals, pressure signals (such as blood pressure, intracranial pressure or cardiac pressure), respiration signals, heart rate signals, pH-level signals, and nerve signals from a nerve such as cranial nerve or a peripheral nerve (such as cuff electrodes on a peripheral nerve). Monitoring elements can include, for example, recording electrodes or various types of sensors.

For example, U.S. Pat. No. 5,995,868 discloses a system for the prediction, rapid detection, warning, prevention, or control of changes in activity states in the brain of a patient. Use of such a closed-loop feed back system for treatment of a nervous system disorder may provide significant advantages in that treatment can be delivered before the onset of the symptoms of the nervous system disorder.

During the operation of a medical device system, the patient is likely to experience multiple detections of the nervous system disorder. For example, in the case of seizures, the patient may have thousands of seizures over the course of a time period, but only a few of those may have behavioral manifestations. The other seizure episodes that don't exhibit behavioral manifestations are considered sub-clinical or electrographic seizures. When the medical device system monitors for seizure occurrences, however, the medical device system may detect many seizure events although only some of these events will spread to other parts of the brain such that the patient will exhibit it (e.g., convulsions, unconsciousness, etc.).

In order to effectively provide treatment therapy, an implanted device may be required to record physiologic data that is related to the disorder. However, an implanted device is typically limited by memory capacity and by battery capacity. Thus, the implanted device is limited in the amount of data that can be processed, stored and reported.

An implanted device may store physiologic data in a data structure and manages memory allocation for the data structure. However, the memory allocation management supported by the implanted device is typically limited. For example, with a FIFO memory buffer if the amount of collected physiologic data exceeds the available memory space, the oldest physiologic data is lost regardless of the importance of the lost data.

It is therefore desirable to selectively store physiologic data in the limited memory space of an implanted device. The implanted device can report the most relevant data from the stored data so that the implanted device can be configured to provide efficacious treatment.

BRIEF SUMMARY

The following represents a simplified summary of some embodiments of the invention in order to provide a basic understanding of various aspects of the invention. This summary is not an extensive overview of the invention nor is it intended to identify key or critical elements of the invention or to delineate the scope of the invention. Its sole purpose is to present some embodiments of the invention in simplified form as a prelude to the more detailed description that is presented thereafter.

In accordance with at least one aspect of the invention, signal data associated with a sensed signal is stored in a circular manner in a set of buffers. A local peak value for the signal data stored in a first buffer is compared to a global peak value. If the local peak value is greater than the global peak value, the global peak value is set equal to the local peak value of the first buffer. Then the signal data is stored into a subsequent buffer. The signal data is checked to see if the local peak value of the subsequent buffer also exceeds the global peak value. If the local peak value does exceed the global peak value, then the global peak value is adjusted to match the local peak value and the above process is repeated in subsequent buffers of the set of buffers in a circular manner as long as the local peak value exceeds the global peak value. This process is repeated until the local peak of the buffer being used to store signal data does not have a local peak value that exceeds the global peak value. When this happens, signal data is stored into a subsequent buffer and if the subsequent buffer does not include a local peak value that exceeds the global peak value, further signal data is stored in the subsequent buffer in a circular manner so that older signal data is overwritten first. In an embodiment, the rewriting of data in the subsequent buffer may continue until the end of the recording period. In another embodiment, an instantaneous peak value may exceed the global peak value and the process of storing signal data in subsequent buffers as discussed above begins again and continues until a local peak fails to exceed the global peak value. Once the recording period is completed, the signal data in the buffers may be archived in another memory for later analysis.

In an embodiment, a window of signal data that begins before and ends after the buffer with the local peak value that is determined to be the global peak value may be archived in a memory. In an alternative embodiment, the window is positioned so as to cover a first buffer that has the local peak value that was the global peak value and to also include two buffers recorded either before or after the first buffer and this window may be archived in a memory.

DETAILED DESCRIPTION OF THE INVENTION

Figure 1:
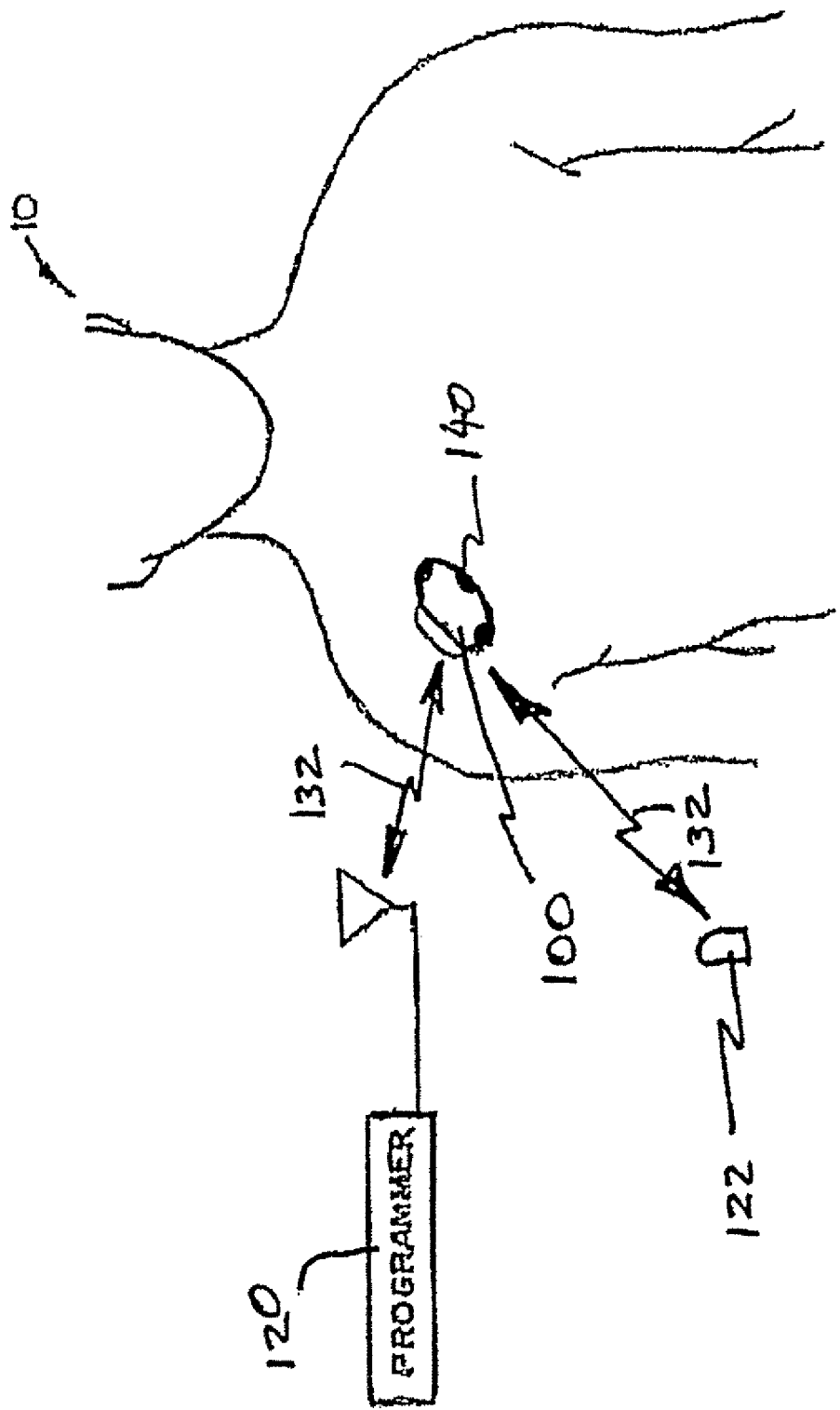
FIG. 1 is a simplified schematic view of a thoracic cavity leadless medical device implanted in a patient that monitors cardiac and respiratory parameters in accordance with an embodiment of the invention.

The following description discloses techniques for selecting, storing and reporting data associated with physiologic signals that may be further associated with a neurological event. These techniques are suitable for use within any implantable medical device system including, but not limited to, a core monitoring device, a full monitoring device, and/or a combination monitoring and treatment device (e.g., involving brain, respiration, and/or cardiac physiologic signals, discussed below). For example, a core monitor system may consist of ECG and respiratory inputs, a full monitor system may consist of ECG, respiratory and EEG inputs, a monitor/treatment system may include brain, cardiac inputs and phrenic nerve stimulation in various combinations.

In an embodiment, the invention is implemented within an implantable neurostimulator system, however, as already discussed, those skilled in the art will appreciate that the techniques disclosed herein may be implemented generally within any implantable medical device system having monitoring capabilities of physiological conditions of the patient including, but not limited to, implantable drug delivery systems, implantable systems providing stimulation and drug delivery, pacemaker systems, defibrillator systems, cochlear implant systems, and implantable diagnostic system for detecting bodily conditions, including those in organs like the brain and/or the heart. The implantable medical device may provide therapeutic treatment to neural tissue in any number of locations in the body including, for example, the brain (which includes the brain stem), the vagus nerve, the spinal cord, peripheral nerves, etc. The treatment therapies can include any number of possible modalities alone or in combination including, for example, electrical stimulation, magnetic stimulation, drug infusion, brain temperature control, and/or any combination thereof.

In addition, the invention may be embodied in various forms to analyze and treat nervous system and other disorders, namely disorders of the central nervous system, peripheral nervous system, and mental health and psychiatric disorders. Such disorders include, for example without limitation, epilepsy, Sudden Unexpected Death in Epilepsy Patients (SUDEP), Parkinson's disease, essential tremor, dystonia, multiple sclerosis (MS), anxiety (such as general anxiety, panic, phobias, post traumatic stress disorder (PTSD), and obsessive compulsive disorder (OCD)), mood disorders (such as major depression, bipolar depression, and dysthymic disorder), sleep disorders (narcolepsy), obesity, tinnitus, stroke, traumatic brain injury, Alzheimer's, and anorexia.

The physiologic signals that are selected, stored and reported in accordance with various aspects of the invention may include any number of sensed signals. Such physiological signals can include, for example, electrical signals (such as EEG, ECoG and/or EKG), chemical signals, biological signals (such as change in quantity of neurotransmitters), temperature signals, pressure signals (such as blood pressure, intracranial pressure or cardiac pressure), respiration signals, heart rate signals, pH-level signals, activity signals (e.g., detected by an accelerometer), and/or peripheral nerve signals (cuff electrodes on a peripheral nerve). Such physiological signals may be recorded using one or more monitoring elements such as monitoring electrodes or sensors. For example, U.S. Pat. No. 6,227,203 provides examples of various types of sensors that may be used to detect a symptom or a condition or a nervous system disorder and responsively generate a neurological signal. In addition, various types of physiologic activities may be sensing including, for example, brain, heart and/or respiration.

As discussed, the techniques disclosed herein are suitable for use within any implantable medical device system including, but not limited to, a core monitoring device, a full monitoring device, and/or a combination monitoring and treatment device. Each of these medical device implementations are discussed in further detail below. In general, however, each of these embodiments utilize one or more monitoring elements that receive signals associated with the physiological conditions being sensed, a memory component that contains multiple data structures (for example, at least one that is age-based and at least one other that is priority-based), and a processing component (logic or software) that stores data records in the data structures as disclosed herein (utilizing, for example, severity and priority determinations for the data).

Core Monitor

In an embodiment, a Core Monitor device monitors cardiac (ECG) and respiration signals and records these signals as discussed herein. Real-time analysis of the ECG signal evaluates rate disturbances (e.g., bradycardia; tachycardia; asystole) as well as any indications of cardiac ischemia (e.g., ST segment changes; T wave inversion, etc.). Real-time analysis of the respiration signal evaluates respiration disturbances (e.g., respiration rate, minute ventilation, apnea, prolonged pauses, etc.). Abnormalities detected during real-time analysis may lead to an immediate patient alert, which can be audible (beeps, buzzers, tones, spoken voice, etc.), light, tactile, or other means. Manual indication of a seizure may be achieved through an external activator device 22. The patient (or caregiver) may push a button on the external device, while communicating with the implanted device. This will provide a marker and will initiate a recording, as discussed herein, of the sensed data (for example, in the event the patient is experiencing a neurological event).

In treating SUDEP, for example, prolonged ECG recordings may be possible (e.g., recording all data during sleep since the incidence of SUDEP is highest in patients during sleep). Post-processing of the signal can occur in the implanted device, the patient's external device and/or some other external device such as the clinician external device. Intermittently (e.g., every morning, once/week, following a seizure) and possibly automatically, the patient or implantable device may download data from the implantable device to the patient external device (as will be discussed further herein), which may then be analyzed by the external device (and/or sent through a network to the physician) to assess any ECG abnormalities. If an abnormality is detected, the device may notify the patient/caregiver. At that time, the patient/caregiver may inform the healthcare provider of the alert to allow a full assessment of the abnormality. The clinician external device may also be capable of obtaining the data from the implanted device and conducting an analysis of the stored signals. If a potentially life-threatening abnormality is detected, the appropriate medical treatment may be prescribed (e.g., cardiac abnormality: a pacemaker, an implantable defibrillator, or a heart resynchronization device may be indicated or respiration abnormality: CPAP, patient positioning, or stimulation of respiration may be indicated).

FIG. 1 is a simplified schematic view of a core monitor 100 implanted in a patient 10. monitor 100 continuously senses and monitors one or more physiological conditions of the patient via monitoring elements 140 (in the embodiment, the physiological conditions are cardiac and respiration functions of patient 10 and the monitoring elements 140 are subcutaneous electrodes). Stored diagnostic data is uplinked and evaluated by an external computing device 120 (e.g. a patient's physician utilizing programmer) via a 2-way telemetry link 132. An external patient activator 122 may optionally allow the patient 10, or other care provider (not shown), to manually activate the recording of diagnostic data.

In the embodiment, monitor 100 encompasses monitoring elements 140 that are several subcutaneous spiral electrodes and may be embedded individually into three or four recessed casings placed in a compliant surround that is attached to the perimeter of implanted monitor 100 as substantially described in U.S. Pat. Nos. 6,512,940 and 6,522,915. These electrodes are electrically connected to the circuitry of the implanted monitor 100 to allow the detection of cardiac depolarization waveforms (as substantially described in U.S. Pat. No. 6,505,067) that may be further processed to detect cardiac electrical characteristics (e.g., heart rate, heart rate variability, arrhythmias, cardiac arrest, sinus arrest and sinus tachycardia). Further processing of the cardiac signals signal amplitudes may be used to detect respiration characteristics (e.g., respiration rate, minute ventilation, and apnea). To aid in the implantation of monitor 100 in a proper position and orientation, an implant aid may be used to allow the implanting physician to determine the proper location/orientation as substantially described in U.S. Pat. No. 6,496,715.

Figure 2:
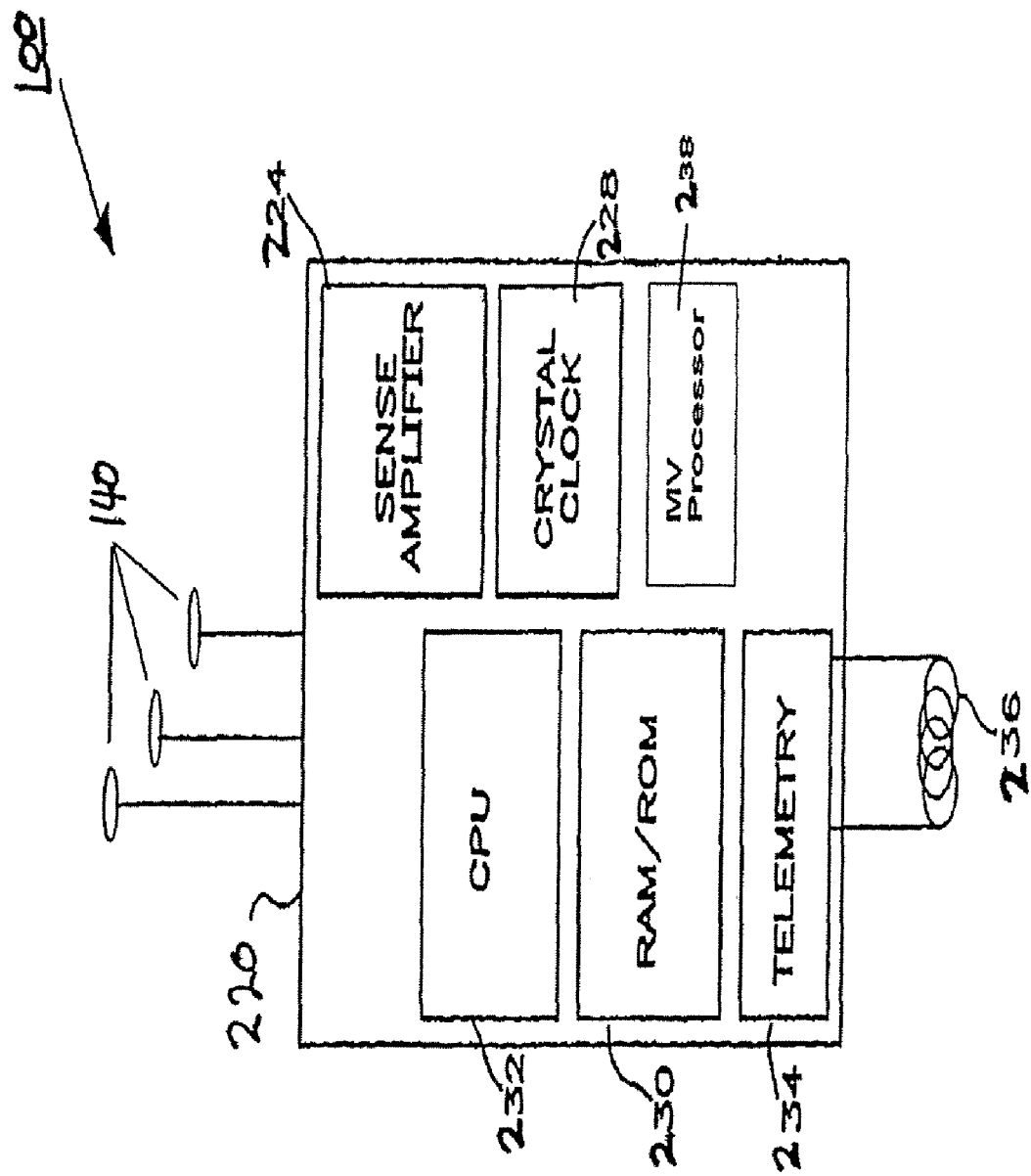
FIG. 2 is a simplified block diagram of a core monitor as shown in FIG. 1.

FIG. 2 depicts a block diagram of the electronic circuitry of the core monitor 100 of FIG. 1 in accordance with an embodiment of the invention. Monitor 100 comprises a primary control circuit 220 and may be similar in design to that disclosed in U.S. Pat. No. 5,052,388. Primary control circuit 220 includes sense amplifier circuitry 224, a crystal clock 228, a random-access memory and read-only memory (RAM/ROM) unit 230, a central processing unit (CPU) 232, a MV Processor circuit 238 and a telemetry circuit 234, all of which are generally known in the art.

Monitor 100 may include internal telemetry circuit 234 so that it is capable of being programmed by means of external programmer/control unit 120 via a 2-way telemetry link 132 (shown in FIG. 1). External programmer/control unit 120 communicates via telemetry with the monitor 100 so that the programmer can transmit control commands and operational parameter values to be received by the implanted device, and so that the implanted device can communicate diagnostic and operational data to the programmer 120. For example, programmer 120 may be Models 9790 and CARELINK® programmers, commercially available from Medtronic, Inc., Minneapolis, Minn. Various telemetry systems for providing the necessary communications channels between an external programming unit and an implanted device have been developed and are well known in the art. Suitable telemetry systems are disclosed, for example, in U.S. Pat. Nos. 5,127,404; 4,374,382; and 4,556,063.

Typically, telemetry systems such as those described in the above referenced patents are employed in conjunction with an external programming/processing unit. Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modeled as an air-core coupled transformer. An example of such a telemetry system is shown in U.S. Pat. No. 4,556,063.

In order to communicate digital data using RF telemetry, a digital encoding scheme such as is described in U.S. Pat. No. 5,127,404 can be used. In particular, a pulse interval modulation scheme may be employed for downlink telemetry, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encode a digital "0" bit while a longer interval encodes a digital "1" bit. For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen-position data frame may be defined, wherein a pulse in one of the time slots represents a unique four-bit portion of data.

Programming units such as the above-referenced Medtronic Models 9790 and CARELINK® programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

As previously noted, primary control circuit 220 includes central processing unit 232 which may be an off-the-shelf programmable microprocessor or microcontroller, but in an embodiment of the invention is a custom integrated circuit. Although specific connections between CPU 232 and other components of primary control circuit 220 are not shown in FIG. 2, it will be apparent to those of ordinary skill in the art that CPU 232 functions to control the timed operation of sense amplifier circuit 224 under control of programming stored in RAM/ROM unit 230. Those of ordinary skill in the art will be familiar with such an operative arrangement.

With continued reference to FIG. 2, crystal oscillator circuit 228, in an embodiment, is a 32,768-Hz crystal controlled oscillator, provides main timing clock signals to primary control circuit 220. The various components of monitor 100 are powered by means of a battery (not shown), which is contained within the hermetic enclosure of monitor 100. For the sake of clarity in the figures, the battery and the connections between it and the other components of monitor 100 are not shown. Sense amplifier 224 is coupled to monitoring elements 140. Where cardiac intrinsic signals are sensed, they may sensed by sense amplifier 224 as substantially described in U.S. Pat. No. 6,505,067.

Processing by CPU 232 allows the detection of cardiac electrical characteristics and anomalies (e.g., heart rate, heart rate variability, arrhythmias, cardiac arrest, sinus arrest and sinus tachycardia). Further processing of the cardiac signals signal amplitudes may be used to detect respiration characteristics/anomalies (e.g., respiration rate, tidal volume, minute ventilation, and apnea) in MV Processor 238.

Figure 3:
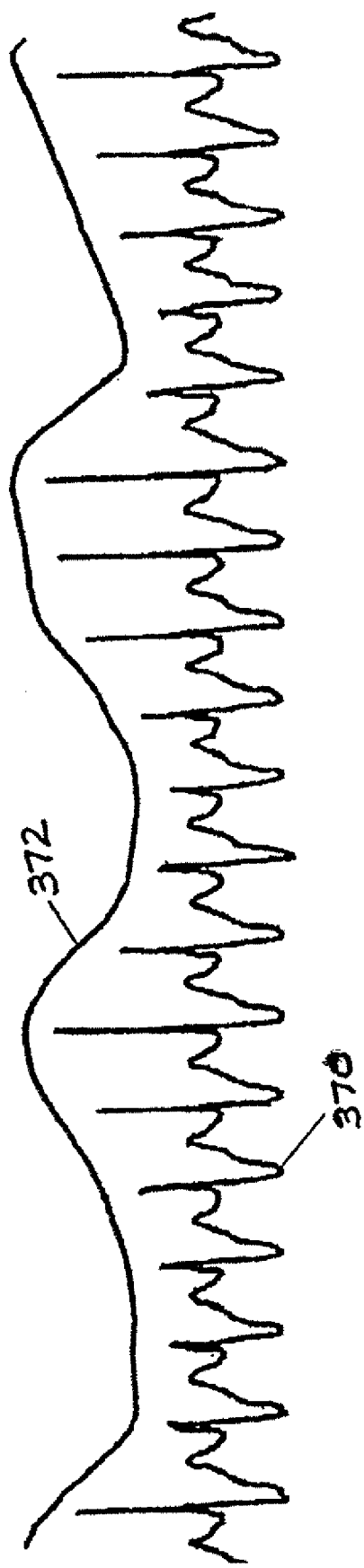
FIG. 3 is a graphical representation of the signals sensed by core monitor as shown in FIG. 1 above.

FIG. 3 shows the intracardiac signals 370 presented to sense amplifier 224 from monitoring elements 140. Note the amplitude variation of cardiac signals caused by the change in thoracic cavity pressure due to respiration (i.e., inspiration and expiration). By low pass filtering the cardiac signals 370, a signal representing minute ventilation may be obtained as depicted in waveform 372. This respiration signal may further be examined to detect respiration rate and reduced or absence of inspiration and expiration (central apnea) by CPU 232 and software resident in RAM/ROM 230.

Upon detection of either a cardiac or respiration anomaly, CPU 232, under control of firmware resident in RAM/ROM 230, will initiate recording of the appropriate diagnostic information into RAM of RAM/ROM 230 (discussed further herein), initiate a warning or alert to the patient, patient caregiver, or remote monitoring location.

Figure 4:
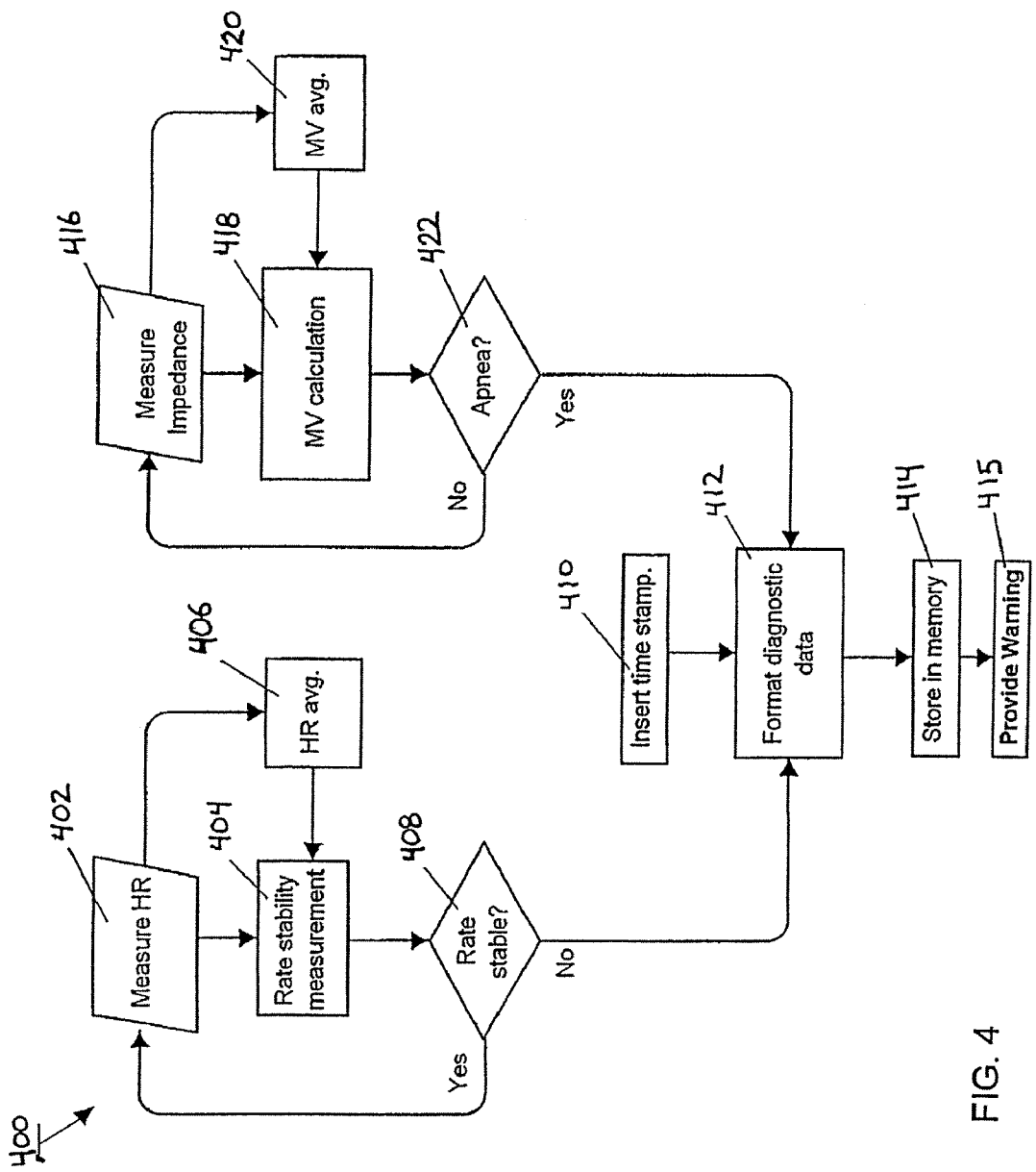
FIG. 4 is a flow diagram showing operation of a core monitor as shown in FIG. 1 above.

FIG. 4 is a flow diagram 400 showing operation of a core monitor sensing/monitoring cardiac and respiration parameters for the detection of a neurological event as shown and described in FIG. 1 above. Beginning at block 402, the interval between sensed cardiac signals are measured. At block 404, a rate stability measurement is made on each cardiac interval utilizing a heart rate average from block 406. At block 408, a rate stable decision is made based upon preprogrammed parameters. If YES, the flow diagram returns to the HR Measurement block 402. If NO, the rate stability information is provided to Format Diagnostic Data block 412.

At block 416, thoracic impedance is continuously measured in a sampling operation. At block 418, a MV and respiration rate calculation is made. At block 422, a pulmonary apnea decision is made based upon preprogrammed criteria. If NO, the flow diagram returns to MV Measurement block 416. If YES, the occurrence of apnea and MV information is provided to Format Diagnostic Data block 412. Format Diagnostic Data block 412 formats the data from the cardiac and respiration monitoring channels, adds a time stamp (i.e., date and time) and provides the data to block 414 where the data is stored in RAM, SRAM or MRAM memory for later retrieval by a clinician via telemetry (using the techniques discussed herein). Optionally, block 412 may add examples of intrinsic ECG and/or respiration signals recorded during a sensed neurological event. Additionally, optionally, block 415 may initiate a warning or alert to the patient, patient caregiver, or remote monitoring location (as described in U.S. Pat. No. 5,752,976).

It will be appreciated that alternative embodiments of the core monitor device may also be utilized. As discussed above, core monitor 100 may sense any number of physiologic conditions of the patient for purposes of detecting, and storing data relating to, any number of the neurological events. For example, cardiac lead(s) may be used to facilitate detection of a neurological event and the recording of data and signals pre and post event. Cardiac leads may consist of any typical lead configuration as is known in the art, such as, without limitation, right ventricular (RV) pacing or defibrillation leads, right atrial (RA) pacing or defibrillation leads, single pass RA/RV pacing or defibrillation leads, coronary sinus (CS) pacing or defibrillation leads, left ventricular pacing or defibrillation leads, pacing or defibrillation epicardial leads, subcutaneous defibrillation leads, unipolar or bipolar lead configurations, or any combinations of the above lead systems.

In another embodiment, an electrode located distally on a sensor stub may be used to facilitate detection of a neurological event and the recording of data and signals pre and post event. The sensor stub is inserted subcutaneously in a thoracic area of the patient. The monitor 100 may sense cardiac signals between an electrode on the distal end of the sensor stub and the monitor case as described in conjunction with the embodiment shown in FIG. 5 in U.S. Pat. No. 5,987,352. The monitor 100 may also sense respiration parameters such as respiration rate, minute ventilation and apnea via measuring and analyzing the impedance variations measured from the implanted monitor 100 case to the electrode located distally on the sensor stub lead as substantially described in U.S. Pat. Nos. 4,567,892 and 4,596,251.

In yet another embodiment, an external wearable device such as a wearable patch, a wristwatch, or a wearable computing device may be used may be used to continuously sense and monitor cardiac and respiration function of patient 10. Optionally, a button on the external wearable device may be activated by the patient 10 (or a caregiver) to manually activate data recording (for example, in the event the patient is experiencing a neurological event). The external wearable device may comprise an amplifier, memory, microprocessor, receiver, transmitter and other electronic components as substantially described in U.S. Pat. No. 6,200,265. In the embodiment of a wearable patch, the device may consist of a resilient substrate affixed to the patient's skin with the use of an adhesive. The substrate flexes in a complimentary manner in response to a patient's body movements providing patient comfort and wearability. The low profile patch is preferably similar in size and shape to a standard bandage, and may be attached to the patient's skin in an inconspicuous location.

Figure 5:
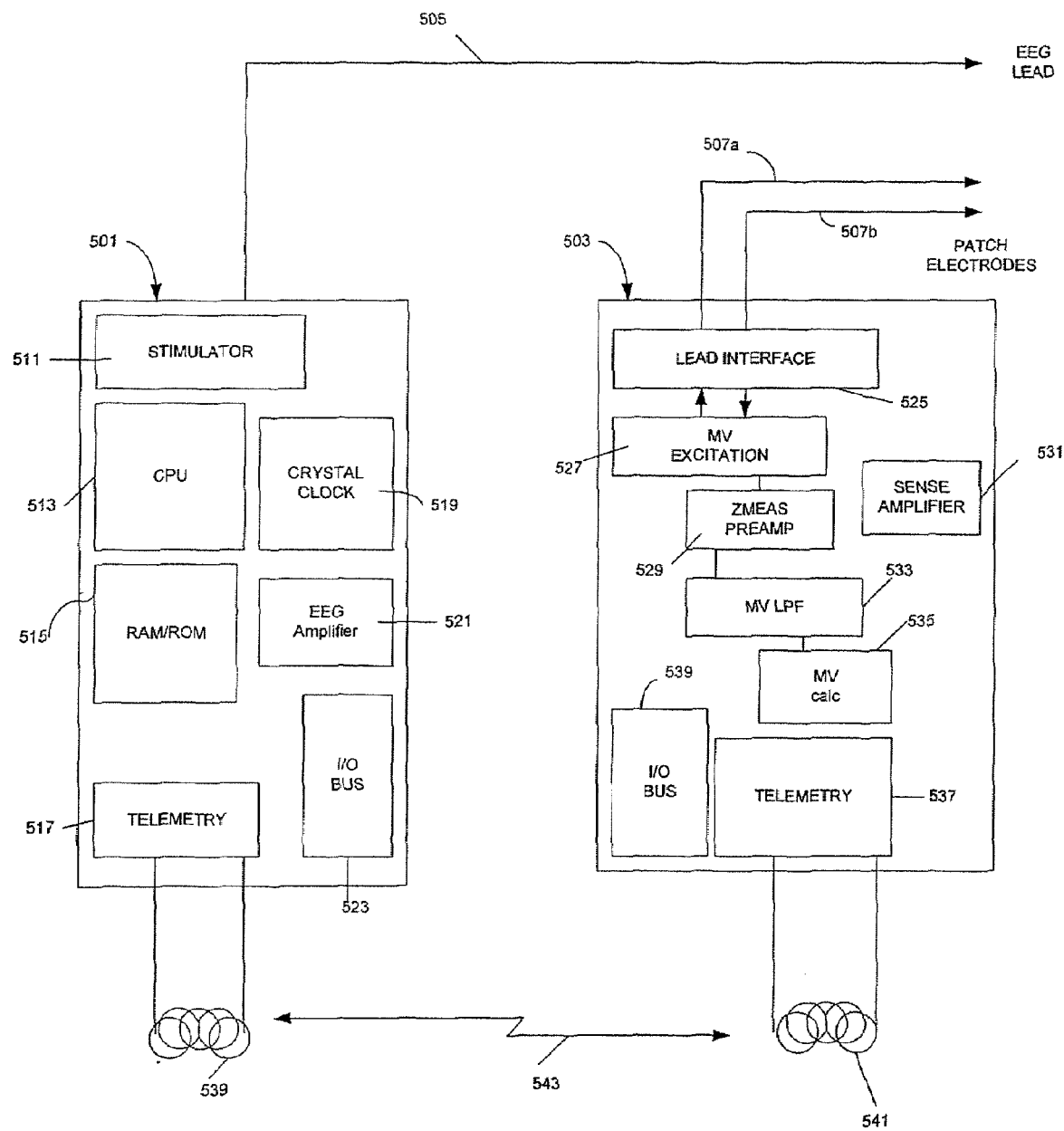
FIG. 5 shows a first apparatus for collecting physiologic data that can be retained in accordance with an embodiment of the invention.

FIG. 5 shows an apparatus 500 for collecting physiologic data that can be retained in accordance with an embodiment of the invention. Apparatus comprises implanted device 501 and external device 503. In the embodiment, implanted device 501 collects physiological data through EEG lead 505, which is coupled to an electrode. The embodiment may support a plurality of electrodes that may collect physiological data from desired locations in the brain or other neural tissue within the body. With respect to sensing of the brain, the embodiment may support electrodes that are positioned in the brain, positioned on the scalp, or a combination. EEG amplifier 521 processes neurological signals from EEG lead 505, while stimulator 511 forms appropriate electrical waveforms to simulate electrodes that are coupled to EEG lead 505. CPU 513 controls the circuitry in internal device 501 and is clocked by crystal clock 519. CPU 513 obtains instructions from and stores neurological data to RAM/ROM 515. Communication within internal device between components is transported on I/O bus 523.

External device 503 collects other physiologic data through patch leads 507a and 507b, which are coupled to patch electrodes. External device 503 is typically worn by the patient. In the embodiment, the patch electrodes monitor and stimulate the respiration of the patient in concert with monitoring neurological data. Respiratory data is collected from the patch electrodes through lead interface 525. Minute Ventilation (MV) module 527 excites the patch electrodes (if necessary) while respiratory data (indicative of the minute ventilation) is obtained through sense amplifier 531. (Minute or total ventilation is the product of respiratory rate and tidal volume.) Additionally, impedance module 529, MV low pass filter 533, and MV calibration module 535 calibrate MV excitation module 527. Data communication within external device 503 is transported on I/O bus 539.

Internal device 501 and external device 503 communicate with each other over telemetry channel 543 through telemetry interfaces 517 and 537 and antennas 539 and 541. However, internal device 501 and external device 503 may communicate using an alternative communications path. For example, I/O bus 535 and I/O bus 539 may be electrically connected through a wired channel.

While the embodiment shown in FIG. 5 collects and retains physiological data and respiratory data, other physiologic data may be collected and retained. For example, apparatus 500 may collect cardiac data and motor coordination data. The embodiment may further correlate the neurological data with the physiological data.

Full Monitor

The full monitor is capable of monitoring cardiopulmonary parameters as in the core monitor described above, and additionally an EEG from an intracranially implanted lead system. This will allow the full monitor to collect cardiovascular, respiratory and neurologic signals in close proximity to detected neurologic events as well as notifying the patient/caregiver of a prolonged event (and/or status epilepticus). Like the core monitor, cardiovascular and respiratory monitoring may occur around a neurologic event (e.g., peri-ictal). The full monitor device may detect the neurological event and analyze the peri-ictal signals and initiate loop recording. The addition of the neurologic monitor allows shorter loop-recording durations since the beginning of the neurological event may be known with greater certainty. In addition, the EEG monitoring may be programmed to provide alerts when a neurologic event has exceeded a pre-determined duration or severity.

Figure 6:
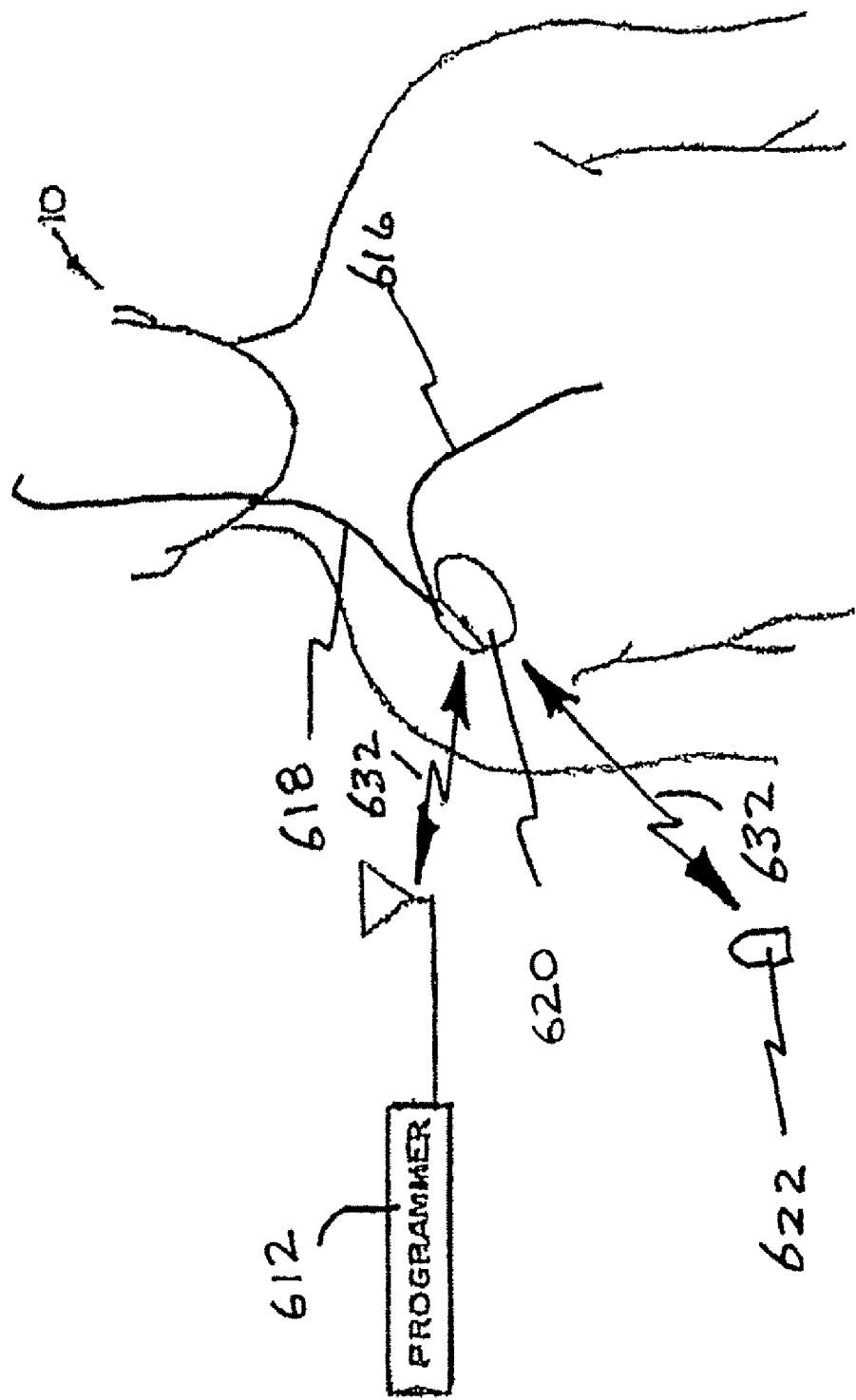
FIG. 6 is a simplified schematic view of an alternative embodiment of a thoracic and cranial leaded medical device implanted in a patient that monitors cardiac, respiratory and brain parameters in accordance with an embodiment of the invention.

FIG. 6 is a simplified schematic view of a full monitor 620 implanted in a patient 10. Monitor 620 continuously senses and monitors cardiac, brain and respiration function of patient 10 via several subcutaneous electrodes 616 and a brain lead 618 to allow detection of neurological events and the recording of data and signals pre and post event. Stored diagnostic data is uplinked and evaluated by the patient's physician utilizing programmer 612 via a 2-way telemetry link 632. An external patient activator 622 may optionally allow the patient 10, or other care provider (not shown), to manually activate the recording of diagnostic data. An implant aid may be used with monitor 620 to ensure a proper position and orientation during implant as described above in connection with the system of FIG. 1.

Figure 7:
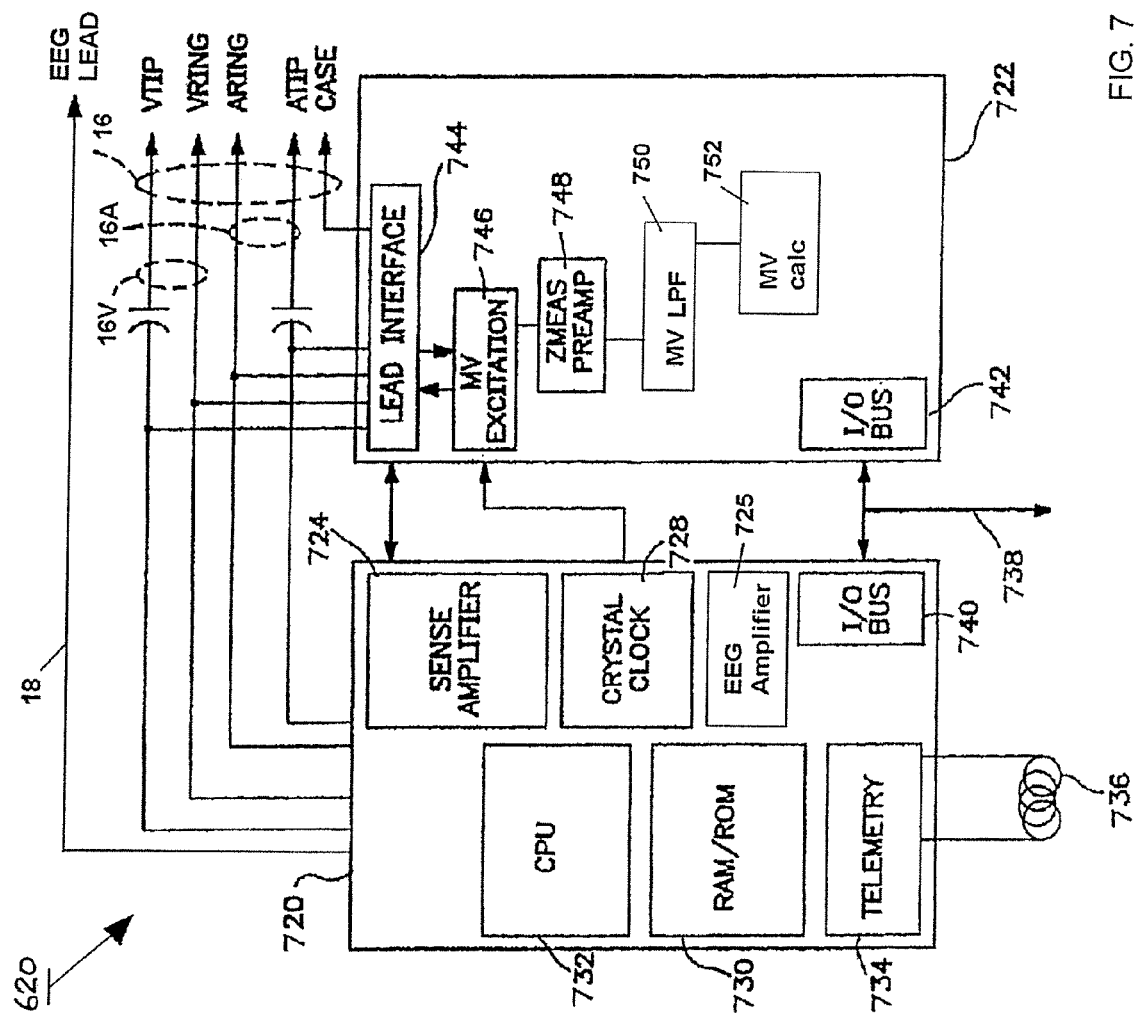
FIG. 7 is a simplified block diagram of a full monitor as shown in FIG. 6 above.

FIG. 7 is a block diagram of the electronic circuitry that makes up full monitor 620 with brain 618 and cardiac 616 leads of FIG. 6 in accordance with the disclosed alternative embodiment of the invention. Monitor 620 comprises a primary control circuit 720 and MV circuit 722 that are described herein above in conjunction with FIG. 2. In addition, the full Monitor 620 also includes an amplifier 725 to amplify and sense EEG signals from a cranially implanted lead 618. The CPU 732, in conjunction with a software program resident in RAM/ROM 730, integrates the information from the sensed cardiac, respiration and EEG signals, detects the onset of cerebral, cardiac and/or respiratory anomalies, formats and stores diagnostic data for later retrieval by the patient's clinician and, optionally, may warn or alert the patient, patient caregiver or remote monitoring location.

Figure 8:
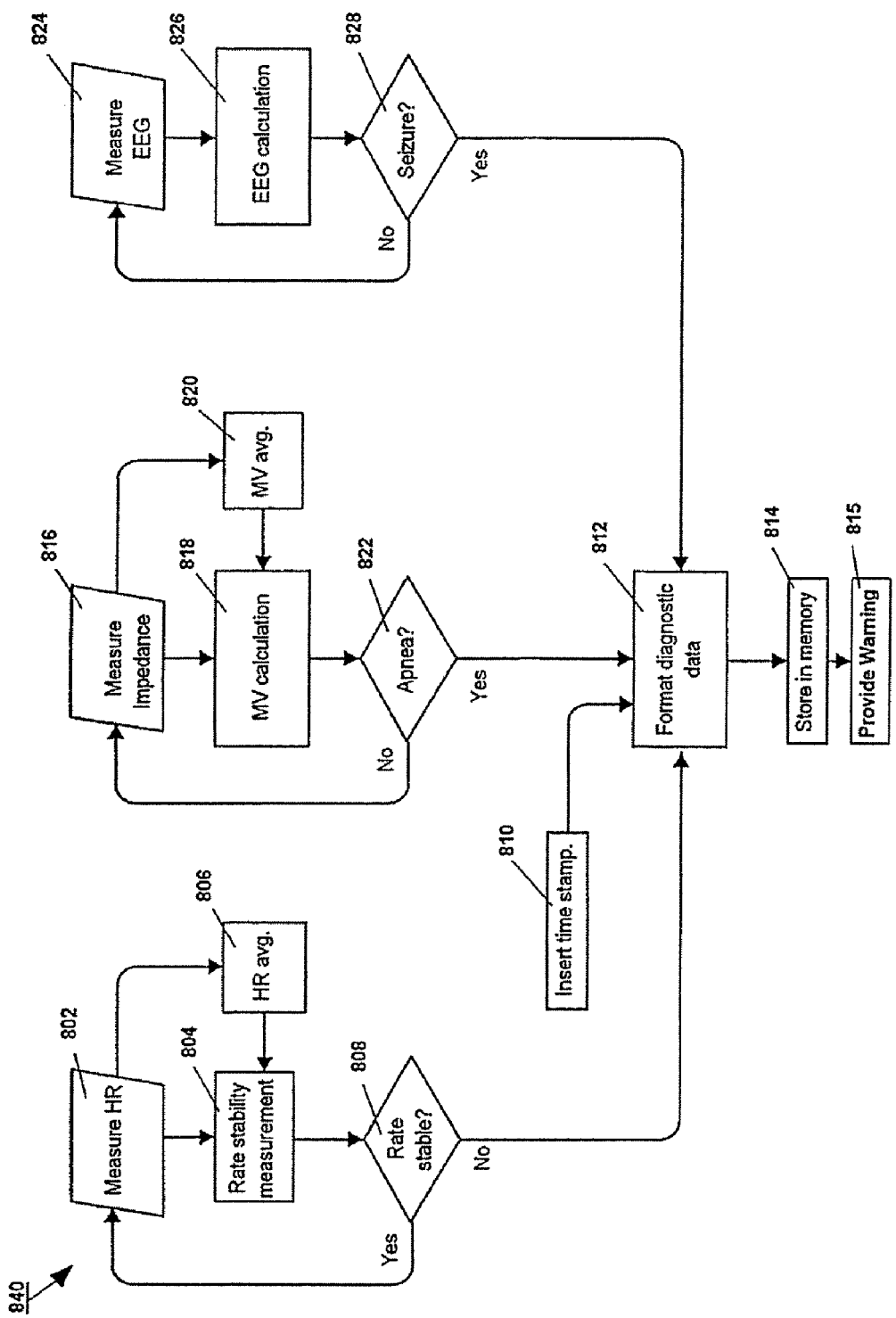
FIG. 8 is a flow diagram showing operation of a full monitor as shown in FIG. 6 above.

FIG. 8 is a flow diagram 840 showing operation of a full monitor sensing and monitoring cardiac, respiration and electroencephalogram parameters for the detection of a neurological event as shown and described in embodiment in FIG. 6 above. Beginning at block 802, the interval between sensed cardiac signals are measured. At block 804, a rate stability measurement is made on each cardiac interval utilizing a heart rate average from block 806. At block 808, a rate stable decision is made based upon preprogrammed parameters. If YES, the flow diagram returns to the HR Measurement block 802. If NO, the rate stability information is provided to Format Diagnostic Data block 812.

At block 816, thoracic impedance is continuously measured in a sampling operation. At block 818, a MV and respiration rate calculation is made. At block 822, a pulmonary apnea decision is made based upon preprogrammed criteria. If NO, the flow diagram returns to MV Measurement block 816. If YES, the occurrence of apnea and MV information is provided to Format Diagnostic Data block 812.

At block 824, the electroencephalogram is sensed and measured. An EEG seizure determination is performed at block 826 as described in U.S. patent application serial no. 2004/0138536. At block 828, a seizure cluster episode is determined. If NO, the flow diagram returns to EEG Measurement block 824. If YES, the occurrence of a seizure cluster is provided to Format Diagnostic Data block 812. Format Diagnostic Data block 812 formats the data from the cardiac, respiration and EEG monitoring channels, adds a time stamp (ie, date and time) and provides the data to block 814 where the data is stored in RAM memory for later retrieval by a clinician via telemetry (using techniques discussed herein). Optionally, block 812 may add examples of intrinsic ECG, respiration and/or EEG signals recorded during a sensed episode/seizure. Additionally, optionally, block 815 may initiate a warning or alert to the patient, patient caregiver, or remote monitoring location (as described in U.S. Pat. No. 5,752,976).

Again, it will be appreciated that alternative embodiments of the full monitor device may also be utilized. For example, cardiac lead(s), a sensor stub, and/or a wearable patch may be used to facilitate detection of a neurologic event and the recording of data and signals pre and post event. An integrated electrode may also be used that senses ECG signals as described in U.S. Pat. No. 5,987,352 and respiration signals as described in U.S. Pat. Nos. 4,567,892 and 4,596,251. Optionally, the monitor may warn/alert the patient 10 via buzzes, tones, beeps or spoken voice (as substantially described in U.S. Pat. No. 6,067,473) via a piezo-electric transducer incorporated in the housing of monitor and transmitting sound to the patient's inner ear.

In another embodiment, the monitor may be implanted cranially in the patient 10. In such an embodiment, the monitor may be constructed as substantially described in U.S. Pat. Nos. 5,782,891 and 6,427,086. EEG sensing may be accomplished by the use of integrated electrodes in the housing of the monitor, cranially implanted leads, and or leadless EEG sensing.

Alternatively, ECG rate and asystole may be inferred using a variety of technologies. For example, ECG rate and asystole may be inferred (along with a blood pressure signal) from a capacitive dynamic pressure signal (i.e., dP/dt) as substantially described in U.S. Pat. No. 4,485,813. Similarly, an acoustic signal (i.e., sound) may be used as substantially described in U.S. Pat. No. 5,554,177 (the sensed acoustic signal is low pass filtered to limit ECG signals to 0.5-3 Hz while filtering out speech, swallowing and chewing sounds). As another example, ECG rate and asystole may be inferred (along with a blood saturation measurement) by monitoring a reflectance oximetry signal (i.e., $O_2$sat) as substantially described in U.S. Pat. No. 4,903,701. As yet another example, a blood temperature signal (i.e., dT/dt) may be used as substantially described in U.S. Pat. No. 5,336,244. As still another example, ECG rate and asystole may be inferred (along with an arterial flow measurement) by monitoring a blood flow signal (from an adjacent vein via impedance plethysmography, piezoelectric sensor or Doppler ultrasound) as substantially described in U.S. Pat. No. 5,409,009. As another example, ECG rate and asystole may be inferred (along with a blood pressure measurement) by monitoring a blood pressure signal utilizing a strain gauge s substantially described in U.S. Pat. No. 5,168,759. As another example, ECG rate and asystole may be inferred by monitoring a blood parameter sensor (such as oxygen, pulse or flow) located on a V-shaped lead as substantially described in U.S. Pat. No. 5,354,318.

Monitor and Treat

As exemplified above, any number of implantable medical device systems are envisioned that may incorporate the recording and retention techniques discussed herein. For example, the monitoring may be achieved using any of the above techniques in conjunction with treatment by delivery of treatment therapy (e.g., electrical stimulation) to the brain, cardiac or respiration.

Figure 9:
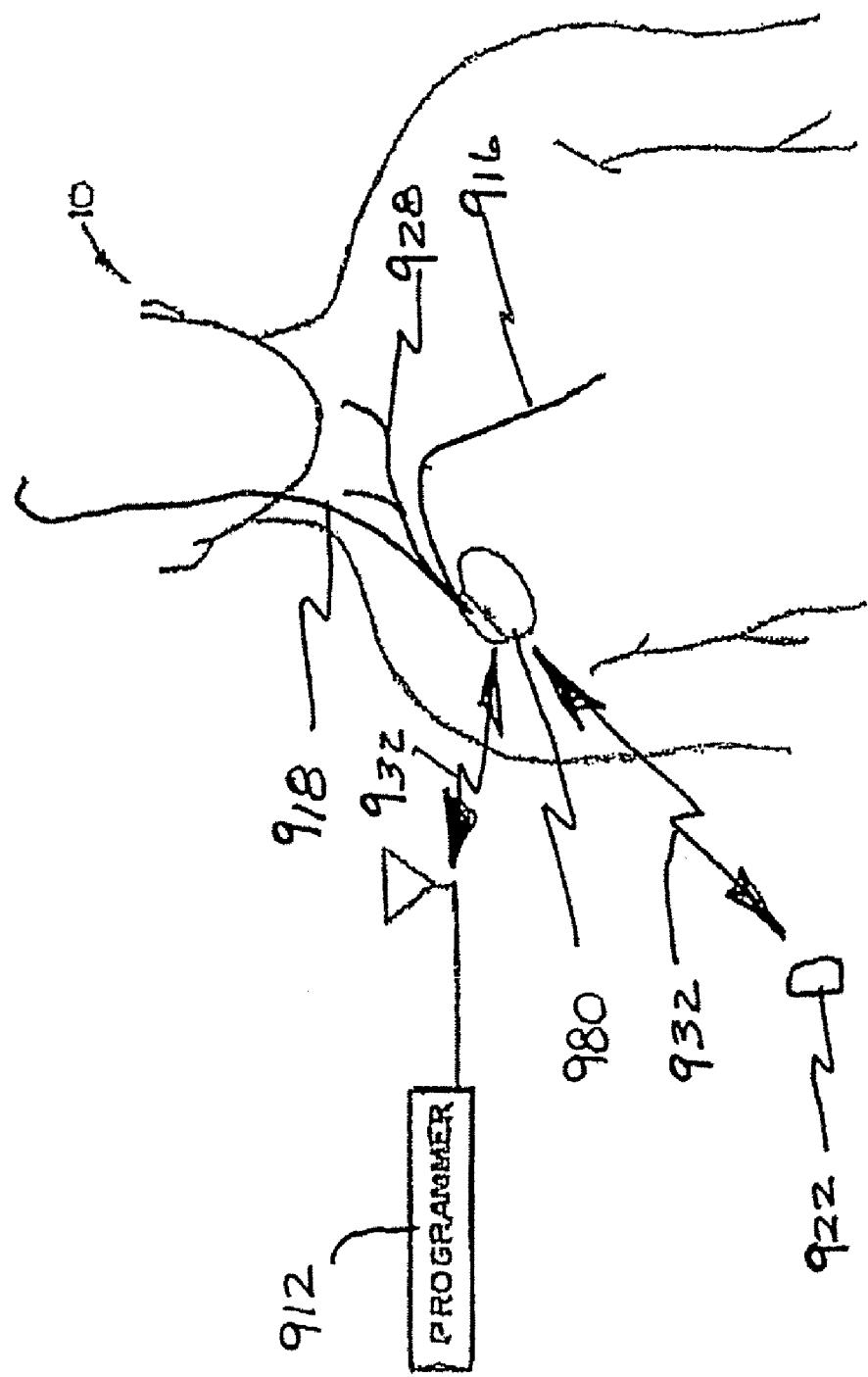
FIG. 9 is a simplified schematic view of another embodiment of a cardiac, cranial and phrenic nerve leaded medical device implanted in a patient that monitors cardiac, respiratory and brain parameters and provides brain, respiration, and cardiac treatment thereof in accordance with an embodiment of the invention.

FIG. 9 is a simplified schematic view of a full Monitor/Brain, Respiration and Cardiac Therapy unit 980 implanted in a patient 10. Monitor/Brain, Respiration and Cardiac Therapy unit 980 continuously senses and monitors cardiac, brain and/or respiration function of patient 10 via cardiac lead(s) 916 and a brain lead 918 to allow detection of epileptic neurological events, the recording of data and signals pre and post event, and the delivery of therapy via brain lead 918, cardiac lead(s) 916 and phrenic nerve lead 928. Stored diagnostic data is uplinked and evaluated by the patient's physician utilizing programmer 912 via a 2-way telemetry link 932. An external patient activator 922 may optionally allow the patient 10, or other care provider (not shown), to manually activate the recording of diagnostic data and delivery of therapy. Optionally, lead 928 may connect to the diaphragm to provide direct diaphragmatic stimulation. As discussed any combination of monitoring and any combination of treatment may be implemented.

Figure 10:
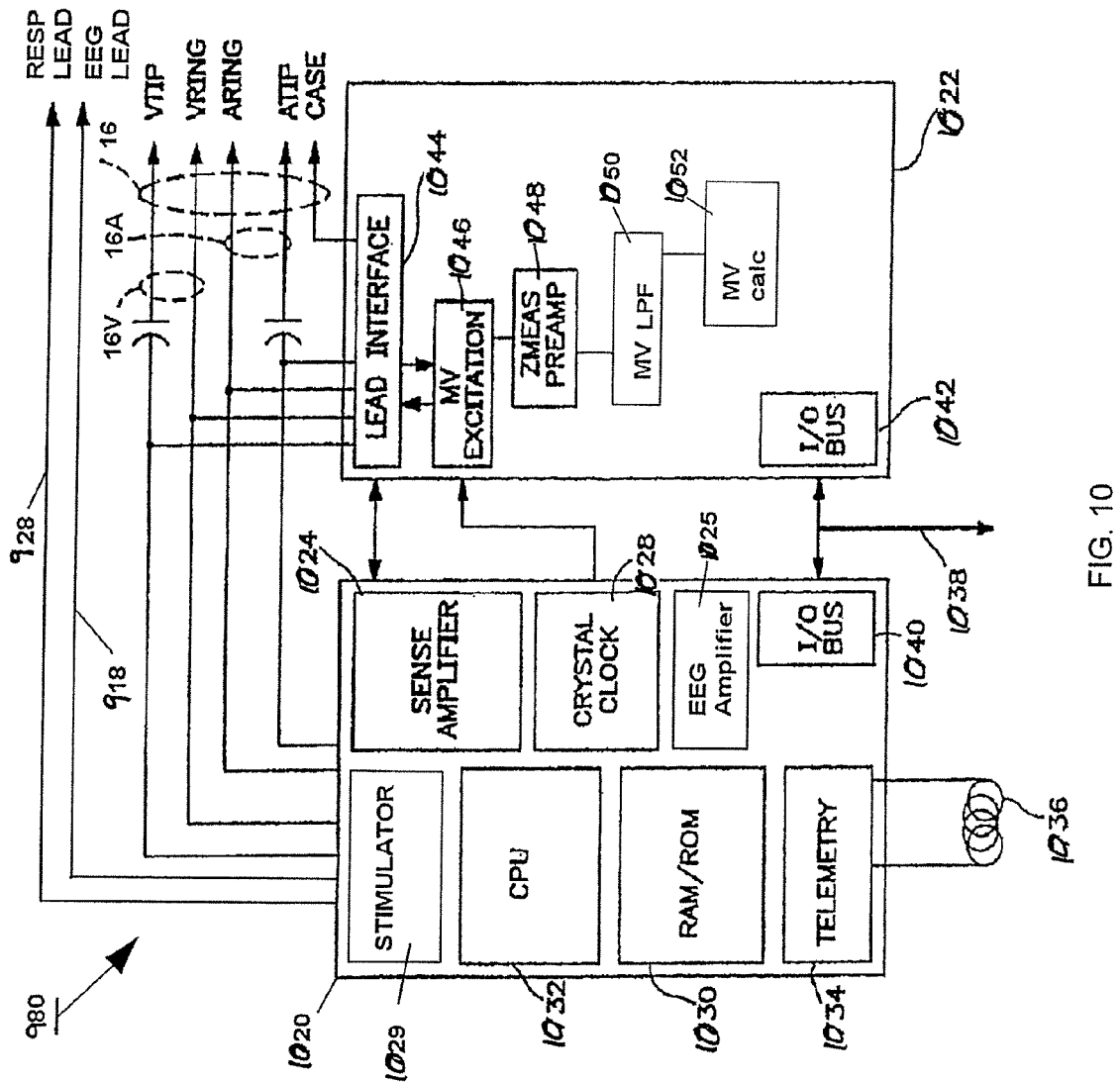
FIG. 10 is a simplified block diagram of a full monitor with brain, respiration and cardiac stimulation therapy as shown in FIG. 9 above.

FIG. 10 is a block diagram of the electronic circuitry that makes up full Monitor/Brain, Respiration and Cardiac Therapy device 980 of FIG. 9. Monitor/Brain, Respiration and Cardiac Therapy device 980 comprises a primary control circuit 1020 and MV circuit 1022 whose function was described herein above in conjunction with FIG. 2. In addition the Monitor/Brain, Respiration and Cardiac Therapy device of FIG. 10 also includes an amplifier 1025 to amplify and sense EEG signals from a cranially implanted lead 918 and an output stimulator 1029 to provide brain stimulation via cranially implanted lead 918 and phrenic nerve stimulation via respiration lead 928. The CPU 1032, in conjunction with software program in RAM/ROM 1030, integrates the information from the sensed cardiac, respiration and EEG signals, detects the onset of cerebral, cardiac and/or respiratory anomalies, provides preprogrammed stimulation therapy to the patient's brain via lead 918, stimulation of the patient's phrenic nerve via respiration lead 928 and stimulation of the patient's heart via cardiac leads 916, formats and stores diagnostic data for later retrieval by the patient's clinician and, optionally, may warn or alert the patient, patient caregiver or remote monitoring location. Optionally, lead 928 may connect to the diaphragm to provide direct diaphragmatic stimulation.

Figure 11:
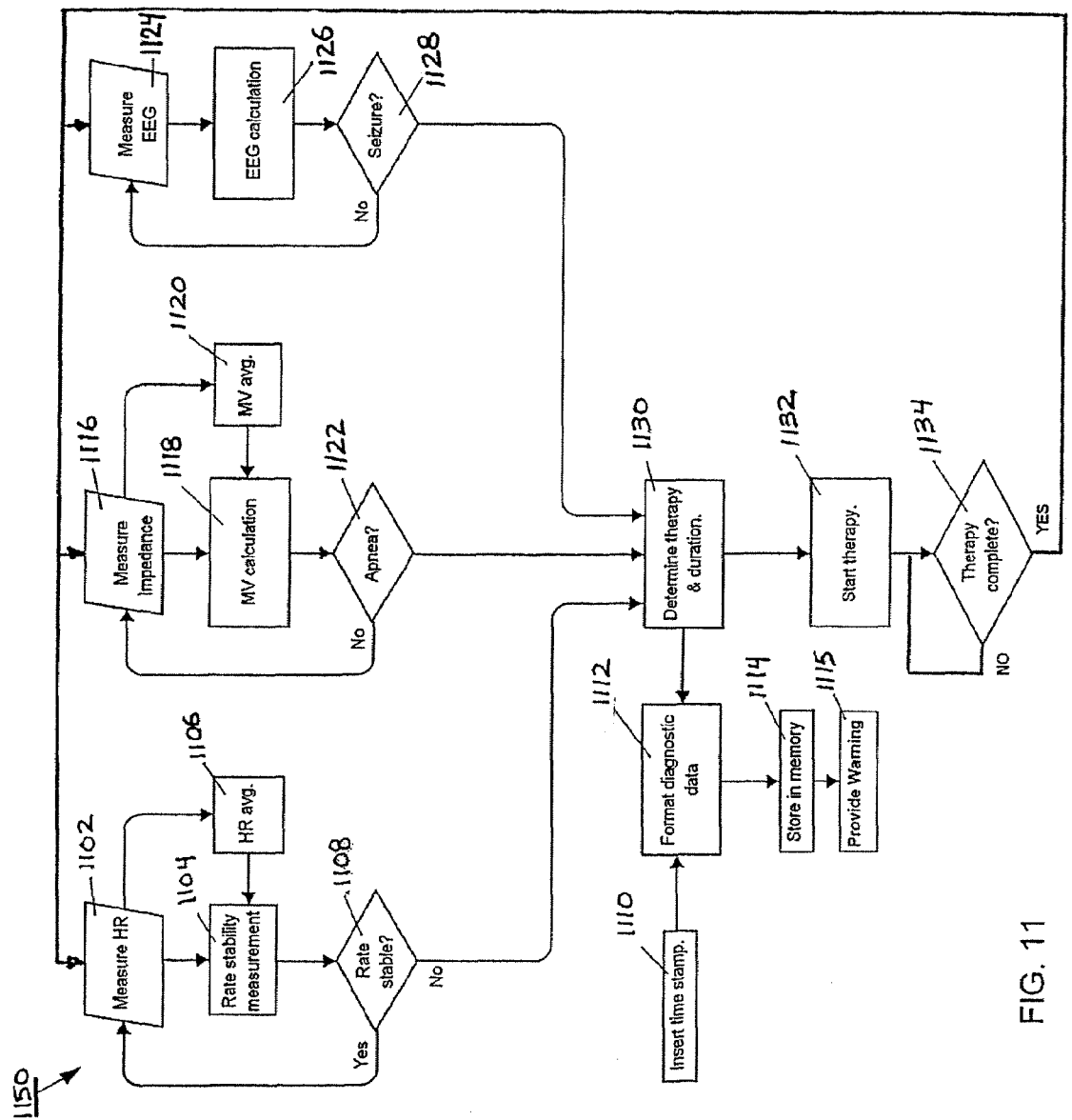
FIG. 11 is a flow diagram showing operation of a full monitor with therapy (including brain, respiration and/or cardiac stimulation therapy) as shown in FIG. 9 above.

FIG. 11 is a flow diagram 1150 showing operation of a full monitor/therapy sensing and monitoring cardiac, respiration and electroencephalogram parameters as shown and described in FIG. 9 above. Beginning at block 1102, the interval between sensed cardiac signals are measured. At block 1104, a rate stability measurement is made on each cardiac interval utilizing a heart rate average from block 1106. At block 1108, a rate stable decision is made based upon preprogrammed parameters. If YES, the flow diagram returns to the HR Measurement block 1102. If NO, the rate stability information is provided to Determine Therapy and Duration block 1130.

At block 1116, thoracic impedance is continuously measured in a sampling operation. At block 1118, a MV and respiration rate calculation is made. At block 1122, a pulmonary apnea decision is made based upon preprogrammed criteria. If NO, the flow diagram returns to MV Measurement block 1116. If YES, the occurrence of apnea and MV information is provided to Determine Therapy and Duration block 1130.

At block 1124, the electroencephalogram is sensed and measured. An EEG calculation is performed at block 1126. At block 1128, a seizure episode is determined. If NO, the flow diagram returns to EEG Measurement block 1124. If YES, the occurrence of a seizure is provided to Determine Therapy and Duration block 1130.

Based upon the data presented to it, Determine Therapy and Duration block 1130 determines the type of therapy and the duration to block 1132, which controls the start of the therapy by evaluating the severity and ranking of each event (i.e., maximum ratio, duration of seizure detection, spread, number of clusters per unit time, number of detections per cluster, duration of an event cluster, duration of a detection, and inter-seizure interval). Block 1134 monitors the completion of the determined therapy. If the therapy is not complete, block returns to block 1134. If the therapy is determined to be complete, block 1134 returns the flow diagram to blocks 1102 (Measure HR), 1116 (Measure Impedance) and 1124 (Measure EEG) to continue the monitoring of cardiac, respiratory and brain signal parameters. Therapy may consist of neural stimulation, cardiac pacing, cardioversion/defibrillation, and drug delivery via a pump or any combination of therapies.

When block 1130 determines that a therapy is to be initiated Format Diagnostic Data block 1112 formats the data from the cardiac, respiration and EEG monitoring channels, adds a time stamp (ie, date and time), type and duration of therapy and provides the data to block 1114 where the data is stored in RAM memory for later retrieval by a clinician via telemetry (using techniques discussed herein). Optionally, block 1112 may add examples of intrinsic ECG, respiration and/or EEG signals recorded during a sensed episode/seizure.

The above embodiments illustrate that the disclosed techniques may be implemented within any number of medical device systems (drug delivery, electrical stimulation, pacemaking, defibrillating, cochlear implant, and/or diagnostic) but configured to retain sensed data records in accordance with the teachings disclosed herein. In general, the implanted medical component utilizes one or more monitoring elements (e.g., electrodes or other sensors), a memory component having a plurality of data structures (and/or data structure types), a processing component (such as a CPU) to process received data for storage in memory as disclosed herein, and a telemetry component.

Data Reporting and Remote Monitoring

Figure 12:
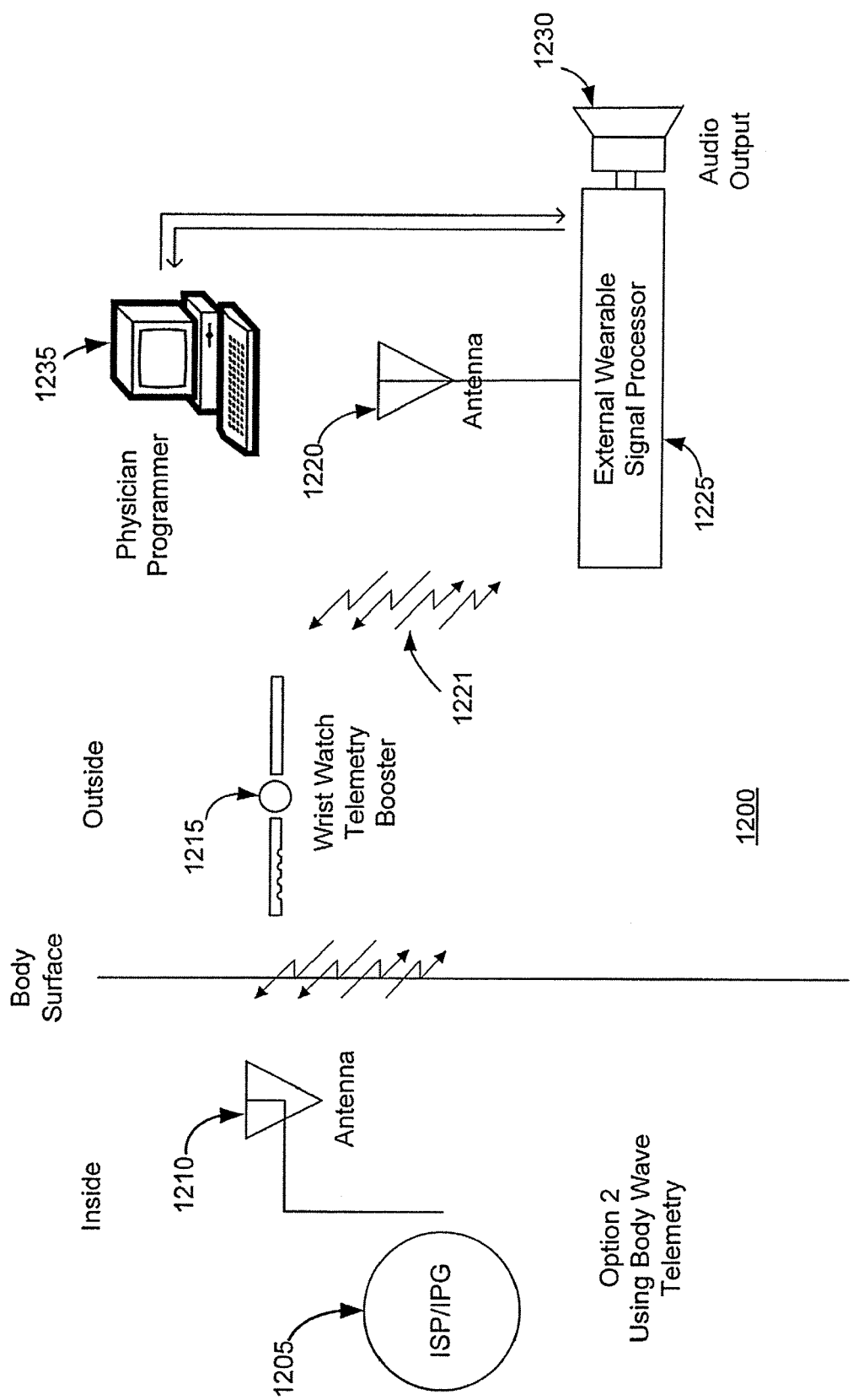
FIG. 12 shows apparatus that supports reporting neurological data in accordance with an embodiment of the invention.

FIG. 12 shows apparatus 1200 that supports reporting physiological data in accordance with an embodiment of the invention. With apparatus 1200, the implanted component 1205 of the medical device system communicates with the relaying module 1215 via telemetry antenna 1210. Similarly, the external component 1225 communicates with the relaying module 1215 via antenna 1220. In the embodiment, a telemetry link 1221 between relaying module 1215 and antenna 1220 comprises a 3 MHz body wave telemetry link. To avoid interference, the relaying module 1215 may communicate with the external and implanted components using differing communication schemes. In some embodiments, the reverse direction and the forward direction of telemetry link 1221 may be associated with different frequency spectra. The relaying module 1215 thereby provides a greater range of communications between components of medical device system. For example, in the embodiment of an implanted system, an external programmer may communicate with an implanted device from a more remote location. The external programmer may be across the room and still be in communication via the relaying module 1215. With the telemetry booster stage, the use of an implanted system is more convenient to the patient, in particular at night while sleeping or when taking a shower, eliminating the need for an external device to be worn on the body. In an embodiment, relating module 1215 may also have the features and functionality of external device 503 as shown in FIG. 5.

Figure 13:
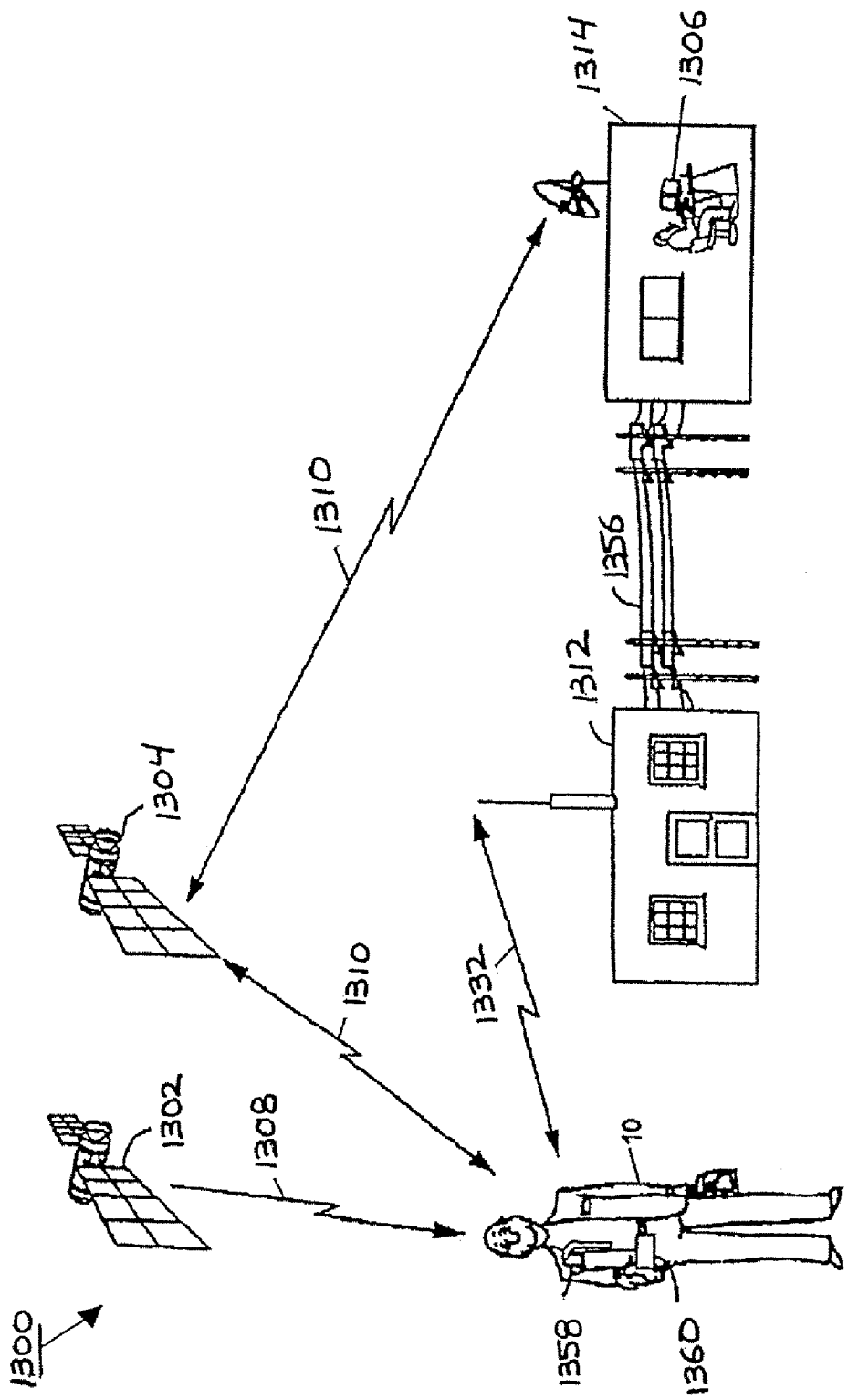
FIG. 13 is a schematic diagram of a system utilizing any of the above-described embodiments and allowing remote monitoring and diagnostic evaluation of at risk patients.

As shown in FIG. 13, in an embodiment, the system allows the residential, hospital or ambulatory monitoring of at-risk patients and their implanted medical devices at any time and anywhere in the world. Medical support staff 1306 at a remote medical support center 1314 may interrogate and read telemetry from the implanted medical device and reprogram its operation while the patient 10 is at very remote or even unknown locations anywhere in the world. Two-way voice communications 1310 via satellite 1304, cellular via link 1332 or land lines 1356 with the patient 10 and data/programming communications with the implanted medical device 1358 via a belt worn transponder 1360 may be initiated by the patient 10 or the medical support staff 1306. The location of the patient 10 and the implanted medical device 1358 may be determined via GPS 1302 and link 1308 and communicated to the medical support network in an emergency. Emergency response teams can be dispatched to the determined patient location with the necessary information to prepare for treatment and provide support after arrival on the scene. See for example, U.S. Pat. No. 5,752,976.

Figure 14:
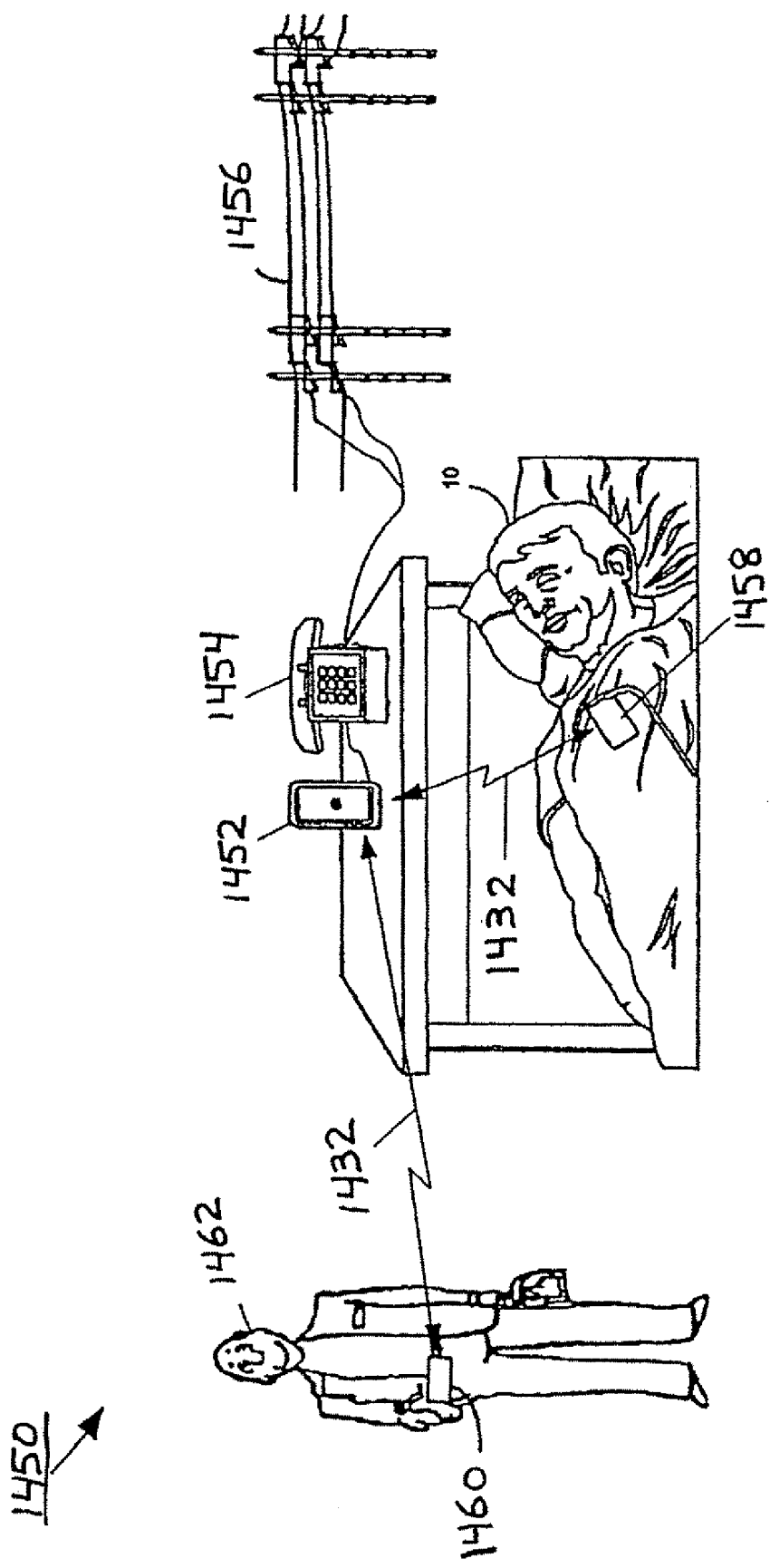
FIG. 14 is a schematic diagram of an alternative system utilizing any of the above-described embodiments and allowing remote monitoring and diagnostic evaluation of at risk patients.

An alternative or addition to the remote monitoring system as described above in conjunction with FIG. 13 is shown in the system 1450 of FIG. 14, which shows a patient 10 sleeping with an implantable Monitor 1458 and/or optional therapy device as described above in connection with the above-described systems. The implantable device 1458, upon detection of a neurologic event may alert a remote monitoring location via local remote box 1452 (as described in U.S. Pat. No. 5,752,976), telephone 1454 and phone lines 1456 or the patient's care provider via an RF link 1432 to a pager-sized remote monitor 1460 placed in other locations in the house or carried (i.e., belt worn) by the care provider 1462. The remote caregiver monitor 1460 may include audible buzzes/tones/beeps, vocal, light and/or vibration to alert the caregiver 1462 of patient's monitor in an alarm/alert condition. The RF link may include RF portable phone frequencies, power line RF links, HomeRF, Bluetooth, ZigBee, WIFI, MICS band (medical implant communications service), or any other interconnect methods as appropriate.

Each of the above embodiments utilized graphical user interfaces that are suitable for displaying data records that have been retrieved from the implantable medical device.

Data Retention and Recording Techniques

Discussed herein are techniques for selecting and storing sensed physiological data in an implanted medical device for subsequent reporting to an external device. As used herein, the term data record encompasses the sensed physiological data, summary information, or simply a pointer that references a location in memory where the sensed physiological data is stored. Thus, the concept of storage of data records in first and second data structures envisions possibilities of storage of the sensed physiological data and the storage of their associated pointers. As an example, summary information data may be stored in the first and second data structures wherein the more detailed and more space consuming waveform data (pre-detection data, post-detection data, etc.) may be stored, and pointed to, in an associated memory (such as a loop record buffer).

Mapping from entries in the first and second data structures to the waveform physiological data that is stored in the associated memory may be achieved with pointers. Each entry in the event log may point to its corresponding waveform data, or each waveform data may point to its corresponding data in the event log. Alternatively, multi-directional pointers in an "allocation table" or "allocation data structure" may be pointed to by the priority structures. Thus, when a data record is overwritten or replaced as discussed herein, both the data record itself and its mapping to the event log may be changed/removed in the allocation structure.

Figure 15:
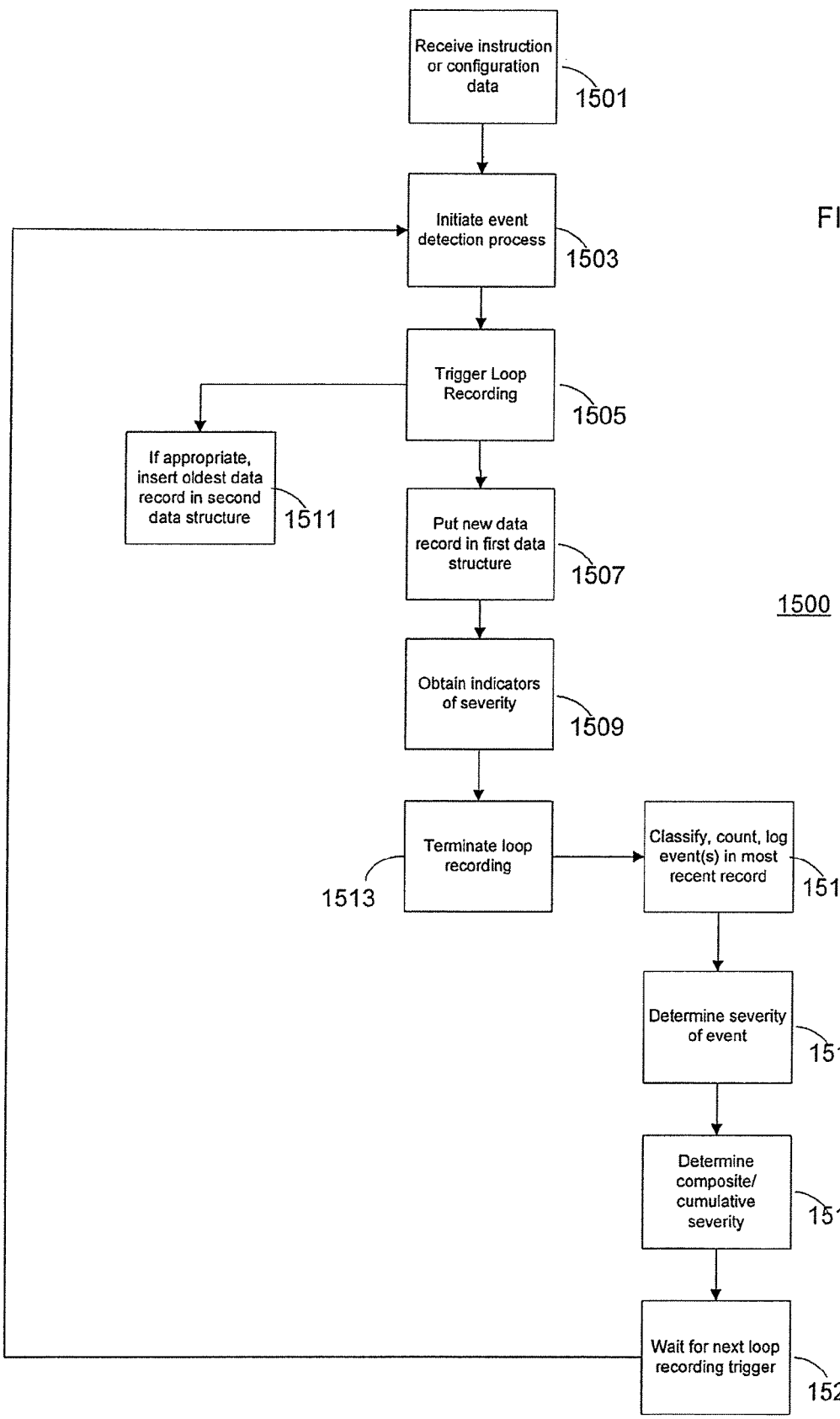
FIG. 15 shows a scenario for storing neurological data in accordance with an embodiment of the invention.

FIG. 15 shows process 1500 for storing physiological data in accordance with an embodiment of the invention. Again, the techniques disclosed herein may be implemented in any of the implantable medical device systems discussed above and may be performed in conjunction with the flow diagrams of FIGS. 4, 8, and 11 above. The process described therein may be implemented by computer executable instructions performed by a processor or dedicated hardware in the form of digital logic gates (also referred as hardware rather than software/firmware) in the implanted device. (Process 1500 may be performed by a logic component that may include a processor and/or digital logic such as an ASIC.) The process described herein discusses the storage of data records within one or more data structures and the moving of those data records. It will be appreciated, however, that these processes may be implemented by storage and movement of pointers, wherein each pointer points to data that is stored in memory, and/or the storage and movement of the sensed physiological data.

The technique for storing data records may begin with step 1501, wherein an implanted device receives an instruction or configuration data from a clinician, typically via telemetry. For example, the clinician or patient may activate loop recording to store data collected for a specified neurological event between a specified time and having a minimum severity level (as will be discussed). In step 1503, an implanted device initiates a detection process for a neurological event. This detection process may implement an event detection algorithm to process the sensed physiological data and determine the possible onset of a neurological event. The neurological event may be associated with a nervous system disorder (e.g., an epileptic seizure) having a severity level and a time duration. The neurological event may also be a cardiac event. For example, a patient's heart rate may increase with an occurrence of an epileptic seizure. Accordingly, the implanted device may initiate loop recording upon determination of a neurological event by processing of sensed physiologic signals or upon determination of any number of other criteria.

By way of example only, the system may monitor one set of physiological signals (e.g., EEG) and trigger loop recording of those same signals upon detection of a neurological event. As another example, the system may monitor any combination of a plurality of physiological signals (including EEG, respiratory, and cardiac) and trigger loop recording of only a subset of those physiological signals based on predetermined criteria being satisfied with respect to one or more of the other physiological signals.

In an embodiment, the implantable medical device may have a set of monitoring elements sensing brain activity and another set of monitoring element that sense a physiological activity other than the brain (e.g., heart activity such as a heart arrhythmia and/or respiratory activity). The device may then implement a detection algorithm to determine the possible onset of a possible neurological event (e.g., a seizure) based on the sensed signals from either the first or second monitoring elements. Once a neurological event is detected, data records associated with the first and second monitoring elements may be stored in memory in accordance with the teachings herein.

Alternatively or additionally, the device may initiate loop recording upon indication to do so by the patient based, for example, on a patient detecting a neurological event. In the event the patient initiates loop recording based on detection of a neurological event (wherein, however, the detection process of the implanted device has not detected the neurological event), the priority index (discussed below) for such data may be set at a higher level such that the data is stored in a memory. In the situation where the patient experiences a neurological event but the medical device has not detected the event, the physiological sensed data may be particularly important for storage and subsequent evaluation. In an embodiment, once activated by a patient, loop recording may save the data for 30 seconds before the indicated seizure and 3 minutes after the seizure. However, to allow for the fact that the patient may not mark the seizure until the seizure has ended, the ECG loop recording may begin before the patient mark. The recording period prior to the patient mark may range from a short time period such as 30 seconds to longer time period such as one hour before the patient mark. This time period may be programmable. As discussed below, a subset or a composite of physiologic channels is selected from the available physiologic channels based on a selection criterion.

Referring still to FIG. 15, if the detected neurological event meets the criterion provided by the clinician, the system triggers loop recording in step 1505. In step 1507, the implanted device stores a data record associated with the sensed physiological data in a first data structure (in an embodiment, a circular buffer as will be discussed in greater detail in FIG. 16). Again, the data record may either be a pointer or the physiological data. An exemplary data entry is discussed below in relation to FIGS. 18 and 19. In an embodiment, the circular buffer stores chronologically sequenced data records in sequential memory locations. When the last location in the circular buffer is reached, the next data record is entered in the first memory location of the circular buffer. Although the embodiment of FIG. 15 and the corresponding discussion herein is with respect to a circular buffer, it will be appreciated that the circular buffer may be any memory device or structure and the data records may be stored and replaced according to an associated priority index (discussed below). When the memory device is full, any new data may replace data in the memory device having the lowest associated priority index. Alternatively, as discussed below, the data may be automatically transferred out once the priority index is calculated.

With the storage of neurological data in step 1507, the implanted device may also obtain and retain indicators of severity when the neurological event occurs in step 1509. Examples of retained indicators include a maximum value of foreground ictal severity and heart rate during the neurological event. Indicators of severity are discussed further below and may be used to determine a priority index.

If the first data structure becomes full, a new data record replaces either the oldest data record or the existing data record having the lowest associated priority index. However, in step 1511, if the associated priority index of the data record being replaced by the new data record is sufficiently large, the data record being replaced may be stored in a priority buffer instead of being permanently removed. It will be appreciated, that the data records may vary in size. Accordingly, for a new data record having a sufficiently large size, the system may require multiple old data record to be removed. Alternatively, only the least important portions of the data record would need to be removed from the first data structure.

The priority index of a data entry, discussed next, is determined in steps 1515, 1517, and 1519 in concert with clinician input and information obtained by the implanted device. In the embodiment of the invention, steps 1507, 1509, and 1511 are executed in a parallel manner. In step 1513, the recording of neurological and other physiological data in the circular buffer is completed. In an alternative embodiment, the data entry may be transferred from the first data structure (such as the circular buffer) to the second data structure (priority buffer) upon the priority index of the data entry being determined. In such an embodiment, the second data structure may begin to be populated with data records without requiring for the first data structure to become full and start replacing older data entries. Since the stored data entry is promptly removed to the second data structure, the circular buffer may vary in size.

One embodiment for determining the priority index of a data record is as follows. In step 1515, the most recent data record is classified. For example, the neurological event may be classified as an epileptic seizure. In step 1517, a priority index of the neurological event is determined. The priority index may be dependent on a severity level. In an embodiment, the severity level is a function of at least one characteristic of the neurological event, including the duration, spread, and measure of ictal content (e.g., peak ratio of algorithmically derived foreground to background ictal score) of the neurological event. Moreover, the embodiment may utilize other derivative indicators for determining the severity level. For example, a binary evidence count may be determined in which each new sample is compared to a criterion (e.g., a threshold determined by the product of a background value and a configured threshold value). If the criterion is met, a value of "1" is inserted into a data structure that contains Y previous Boolean values. Otherwise, if unmet, a value of "0" is inserted into the data structure. Upon insertion, a second value is removed from the data structure to ensure that the data structure retains a size of Y bits. The Boolean value of the first sample is then compared to the Boolean value of the second sample. The difference is used to maintain a separate counter value which reflects how many Boolean values in the data structure (e.g., Y-bit buffer) are "1". In this way, the evidence count reflects the number of samples out of the last Y samples which met the threshold criterion, and therefore ranges from 0 to Y.

As another example, a slew-rate limited output of an associated physiologic channel may be determined by incrementing the slew-rate limited output by a small amount if the sample is greater than the current value of the slew-rate limited output. Otherwise, the slew-rate limited output is decremented by the small amount. The severity level may be determined from the maximum value of the evidence count or the slew-rate limited output associated with the set of physiologic channels contained in a data record.

In addition, the priority index of the neurological event may be dependent on an associated event, e.g. a cardiac event or a user signal in the form of telemetry, presence of a medical magnet, and so forth. In an embodiment, the priority index is stored in a data field in the data record. However, another embodiment of the invention may store the priority index in an associated data structure or may be calculated when it is needed.

In step 1519, a composite severity measure of a group of neurological events, which includes the current neurological event, is determined. The composite severity measure may be a function of determined severity levels of individual events and the relative chronological occurrence of events. For example, a group of epileptic seizures that occur within a short period time may be indicative of a more significant cumulative event than a single epileptic seizure.

While the embodiment illustrated in FIG. 15 shows a sequential ordering of steps, it will be appreciated (as discussed above) that the process may execute the steps in a different order or may execute some of the steps in a parallel fashion.

The priority index may be dependent on the severity level, which may be expressed as a function $f(x_1, x_2, \ldots, x_n)$, and/or on associated factors, which may be expressed as a function $g(y_1, y_2, \ldots y_m)$. Variable $x_i$ corresponds to a characteristic of a physiologic event (e.g., a neurological event), and variable $y_j$ is an associated factor. For example, characteristics of a neurological event may include a duration of a neurological cluster, a spread of a neurological cluster (which may be measured by the number of electrodes detecting the cluster), a statistic of an associated neurological signal, and an event class. A statistic may be a computed quantity characteristic of a physiologic signal or an ensemble of physiologic signals. An event class may include a most-severe seizure (potentially correlating to status epilepticus), a severe seizure, a subclinical seizure, a least severe seizure (potentially correlating to what is more likely to be an erroneous detection), a brady event, a tachy event, arrhythmia, and a detection on each electrode channel.

An associated event may include external event information and associated physiologic information that are correlated to a neurological event. For example, the associated physiologic information may be the age of the event. As another example, an external event may be a cardiac event, a chemical event, a scheduling event, a patient-initiated event (through a physical interface, e.g., a magnet interface or a telemetry interface), a caregiver-initiated event (e.g. through a telemetry channel), and a device-based event. Associated physiologic information may include heart rate, blood pressure, breathing rate, and glucose level. Moreover, an external event may not be associated with a neurological event. For example, a physician may instruct, through a programmer, that physiologic data for a designated time be stored and reported.

The priority index may be expressed as a mathematical combination of the severity level function $f(x_1, x_2, \ldots, x_n)$ and the associated factor function $g(y_1, y_2, \ldots y_m)$. For example, the priority level may be expressed as:

$$\text{priority index} = f(x_1, x_2, \ldots, x_n) + g(y_1, y_2, \ldots y_m) \quad \text{(EQ. 1A)}$$

Either $f(x_1, x_2, \ldots, x_n)$ or $g(y_1, y_2, \ldots y_m)$ may be a continuous function, a discrete-value function, a Boolean function, or a combination of the above function types. As another example, the priority level may be expressed as:

$$\text{priority index} = f(x_1, x_2, \ldots, x_n) \cdot g(y_1, y_2, \ldots y_m) \quad \text{(EQ. 1B)}$$

The priority index may be more generally expressed as a function $h(z_1, z_2)$, where $$\text{priority index} = h(f(x_1, x_2, \ldots, x_n), g(y_1, y_2, \ldots y_m)) \quad \text{(EQ. 1C)}$$

Figure 16:
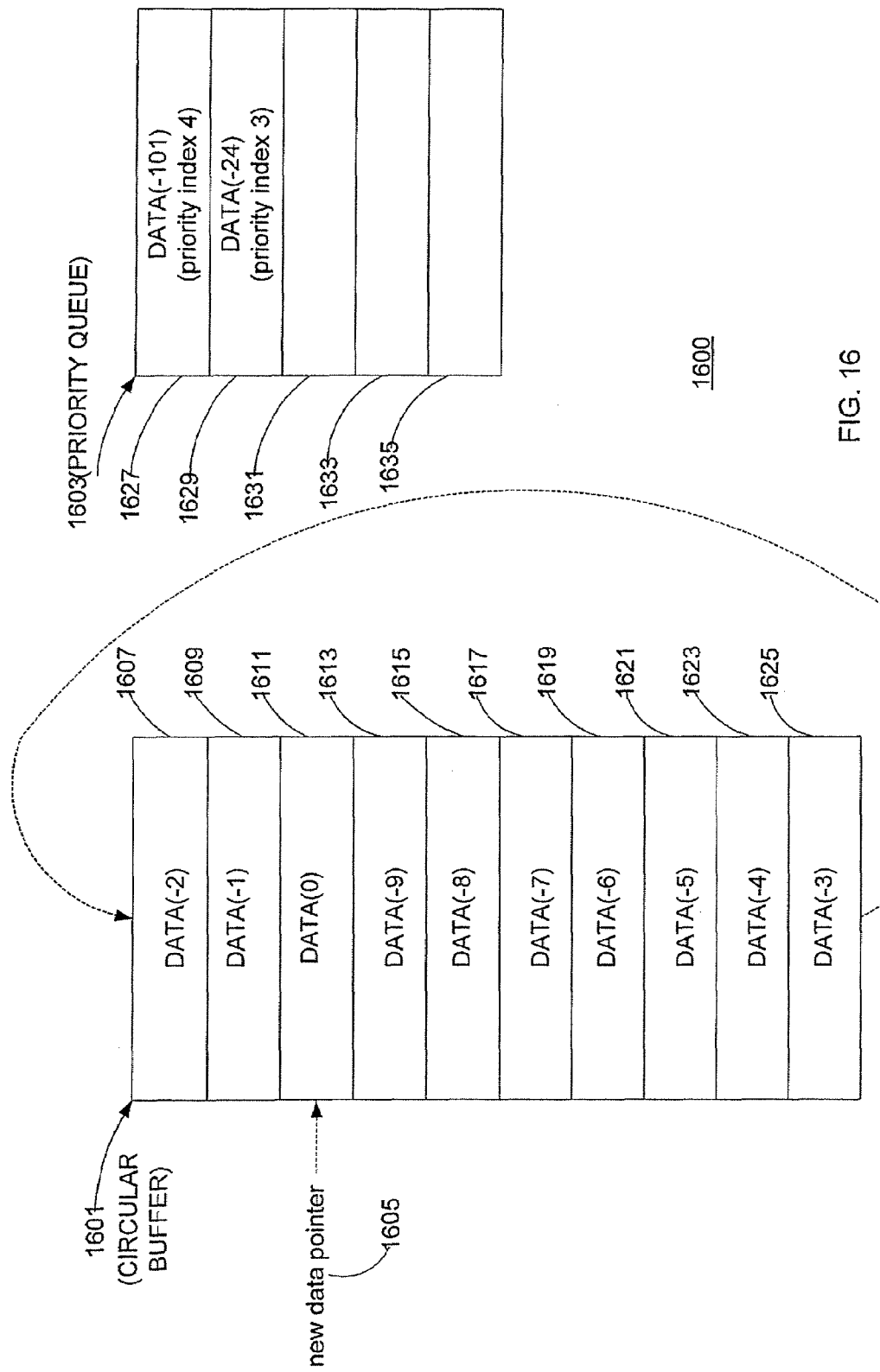
FIG. 16 shows a data structure for storing neurological data in accordance with an embodiment of the invention.

FIG. 16 shows data structure 1600 for storing physiological data in accordance with an embodiment of the invention. In this embodiment, data structure 1600 includes circular buffer 1601 and priority queue 1603. (Another embodiment of the invention may implement circular buffer 1601 and/or priority queue 1603 as a different type of data structure.) Circular buffer 1601 stores the most recent ten data records (DATA(-2) to DATA(-3)) corresponding to data entries 1607-1625). (An exemplary record is discussed with FIG. 18.) However, the embodiment may store a different number of data records, depending on the allocated memory for circular buffer 1601. In the example shown, circular buffer 1601 currently stores data records that have been acquired between the previous nine time units (corresponding to data record DATA(-9)) and the current time (corresponding to data record DATA(0)). New data pointer 1605 points to a data entry in circular buffer 1601. At the current time, new data pointer 1605 points to the data entry where new data is stored. Previous to storing data record DATA(0), data entry 1611 stored data record DATA(-10), which was previously acquired 10 time units ago. The new data record may be associated with physiologic signals and may be further associated with a neurological event. With the next subsequent data acquisition, new data pointer 1605 will point to the next data entry that currently stores data record (DATA(-9)). In the embodiment, the new data record is stored in the data entry that stores the oldest data record. When last data entry 1625 (currently corresponding to data record DATA(-3)) of circular buffer 1601 is reached, the subsequent data acquisition is stored in data entry 1607 currently storing data record DATA(-2).

As discussed, the data record may be the sensed physiological data or a pointer that references a location in memory where the sensed physiological data is stored. Thus, the concept of storage of data records in first and second data structures envisions both possibilities of storage of the sensed physiological data and the storage of their associated pointers. Also as discussed, circular buffer 1601 may be in the form of any other data structure. In such an alternative embodiment, physiological data may be stored in a memory device such that when a new data record is to replace an existing data record, the data record with the lowest priority index is replaced. Alternatively, the data entries being replaced may vary depending on the relative sizes of the new and old data entries.

When a data record has been overwritten by the new data record, a portion of the old data record (which may be the entire data record) is stored in priority queue 1603 if the corresponding priority index is sufficiently large or exceeding a threshold criterion. In one embodiment, the more significant the corresponding physiologic event, the larger the corresponding priority index. However, in another embodiment the priority level may decrease with the significance of the physiologic event. Priority queue 1603 is capable of storing data records in data entries 1627-1635; however, as shown in the example, priority queue 1603 currently stores two data records. The remaining data entries 1631-1635 are empty and may store subsequent data acquisition. Data entry 1627 is currently storing data record DATA(-101), which was acquired 101 time units ago, and data entry 1629 is currently storing data record DATA(-24), which was acquired 24 time units ago. For example, the priority index must have a value of 3 or higher in order to be stored in priority queue 1603 when the corresponding data record is overwritten in circular buffer 1601. In the event that the priority queue 1603 is also filled, the system may determine that a data record shall be retained in priority queue 1603 only if the priority index of the removed data record from circular buffer 1601 has a larger priority index than any of the stored data entries in priority queue 1603. In other embodiments, the system may utilize a combination of the above retention strategies or other strategies.

In an embodiment of the invention, a data record (stored in data entries 1607-1625) in circular buffer 1601 may contain a different amount of data than a data record (stored in data entries 1627-1635) in priority queue 1603. For example, data may be discarded to reduce the precision or to discard physiologic data that is not directly associated with a neurological event (e.g., cardiac data).

In an embodiment of the invention, stored data (either stored in circular buffer 1601, or priority queue 1603, or both) may be selected in accordance with a retention policy in order to support intelligent data loss (data triage) or offloading (e.g., to an external device) and to conserve memory usage and reduce/bound the time required to transfer the data. For example, an implanted device may store data in data structure 1600 for sensor channels fulfilling a predetermined criteria, may discard waveform data while retaining statistics, summary data, or burden information, enable or disable or prioritize sensor channels based on algorithm criteria, sensor location, or sensor type, or override the retention policy when a clinician provides instructions over a telemetry channel. Moreover, the embodiment may further use data compression if the data is compressible to compress the data content of the new or old record.

Reporting Physiological Data

In accordance with another aspect of the invention, in response to an instruction from a clinician, an implanted device organizes stored physiological data according to the associated priority index and reports a predetermined number of data records that are deemed as having a higher priority index than the other stored data records. Such structures for reporting stored physiological data are disclosed in FIGS. 12-14.

Figure 17:
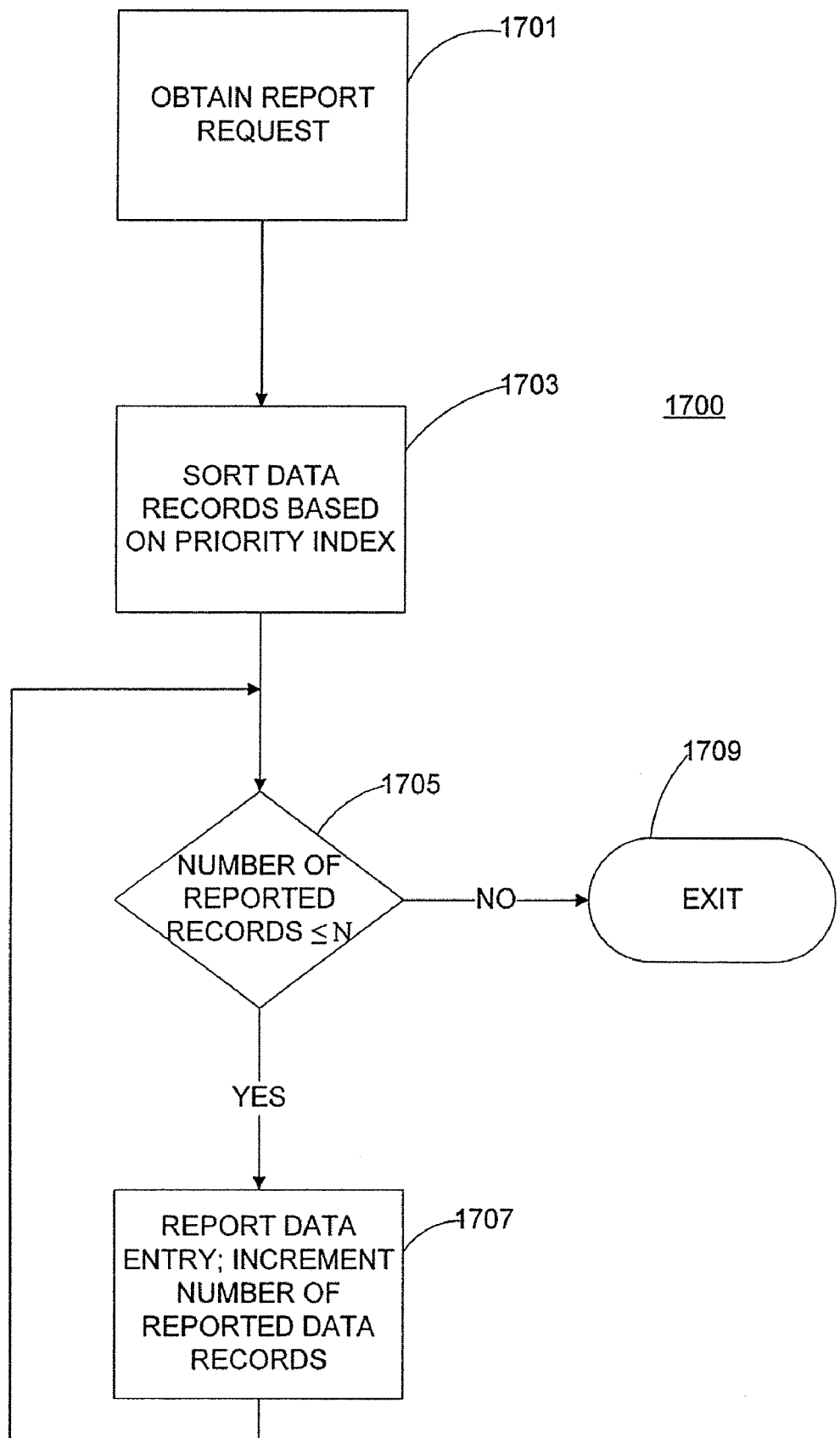
FIG. 17 shows a flow diagram for reporting neurological data in accordance with an embodiment of the invention.

FIG. 17 shows flow diagram 1700 for reporting physiological data in accordance with an embodiment of the invention. Step 1701 corresponds to an implanted device receiving a request (e.g., through a telemetry communications channel).

In step 1703, the data records (both in circular buffer 1601 and priority queue 1603) are sorted according to the associated priority index if the associated priority index is sufficiently large (e.g., three or higher). Step 1705 determines if the number of reported data records is less than or equal to N. N can be, for example, the number of records that the user wishes to retrieve. If so, the physiological data associated with the data record is reported to a clinician's workstation over the telemetry communications channel and the number of reported data is incremented in step 1707. Step 1705 is then repeated. If the number of records is greater than N, the reporting of neurological data is terminated in step 1709, and procedure 1700 is completed.

A physician may request physiological data associated with N data records that are stored in circular buffer 1601 and priority queue 1603 and having a minimum priority index to be reported to, for example, a physician programmer over a telemetry link. The physician programmer may thereby display the requested physiological data or at least those where the priority index is above a threshold. When so instructed, implanted device sorts the physiological data associated with the data records in circular buffer 1601 and priority queue 1603 and reports physiological data associated with the N data records having at least the minimum priority index. Once the data is reported, the implanted device may release the memory space previously allocated to the identified data records, mark that memory space for deletion, and/or delete the data records. If more than N data records have the minimum priority index, the implanted device may select N data records based on a temporal criterion (e.g., the most recent or the oldest), being greater than a predetermined priority index, or a priority index that is dependent on an external event. Moreover, system may select a data record so that each occurring event type is included in the reported data records. Because the invention may be implanted within any implantable medical device system, however, it will be appreciated that the external components may vary in configuration, components and/or features.

Data Format

Figure 18:
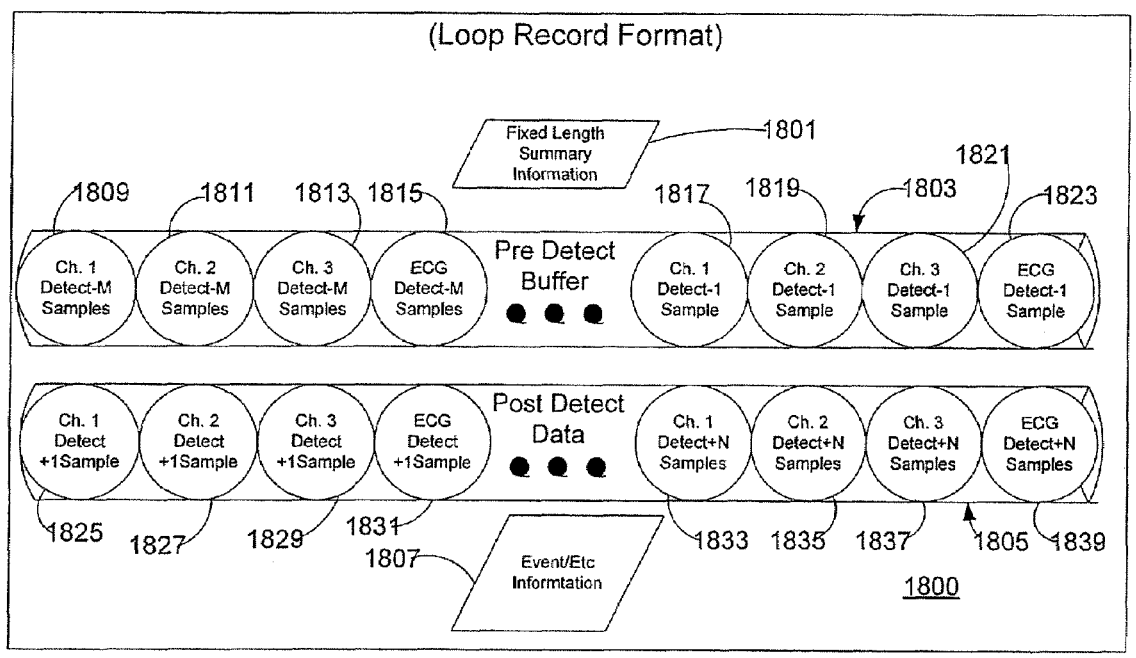
FIG. 18 shows an exemplary data entry that contains physiologic data and that may be retained in memory of an implantable medical device.

FIG. 18 shows exemplary physiological data 1800 that can be retained in implanted medical device. The physiological data 1800 comprises summary information data 1801, pre-detection data 1803, post-detection data 1805, and event/etc information data 1807. Pre-detection data 1803 contains sampled data 1809-1823 that is collected before a detected physiologic event such as an epileptic seizure. Post-detection data 1805 contains sampled data 1825-1839 after the detected physiologic event. In the exemplary data shown in FIG. 18, pre-detection data 1803 includes sampled data 1809 and 1817 that are obtained from neurological channel 1, sampled data 1811 and 1819 that are obtained from neurological channel 2, sampled data 1813 and 1821 that are obtained from neurological channel 3, and sampled ECG data 1815 and 1823 that are obtained from the ECG channel. Post-detection data 1805 includes sampled data 1825 and 1833 that are obtained from neurological channel 1, sampled data 1827 and 1835 that are obtained from neurological channel 2, sampled data 1829 and 1837 that are obtained from neurological channel 3, and sampled data 1831 and 1839 that are obtained from the ECG channel. While the physiologic channels sampled before and after the physiologic event are same in exemplary record 1800, different physiologic channels may be sampled before and after the physiologic event. Additionally, summary information data 1801 contains summary information about record 1800. The embodiment of the invention supports physiological data that has a fixed length or that has a variable length. Event/Etc information data 1807 includes information about the associated physiologic event type and other associated information. Although depicted as data from different channels interleaved together, such data may also be stored in a non-interleaved fashion. For example, ECG may be stored separately from the other channels, etc.

Figure 19:
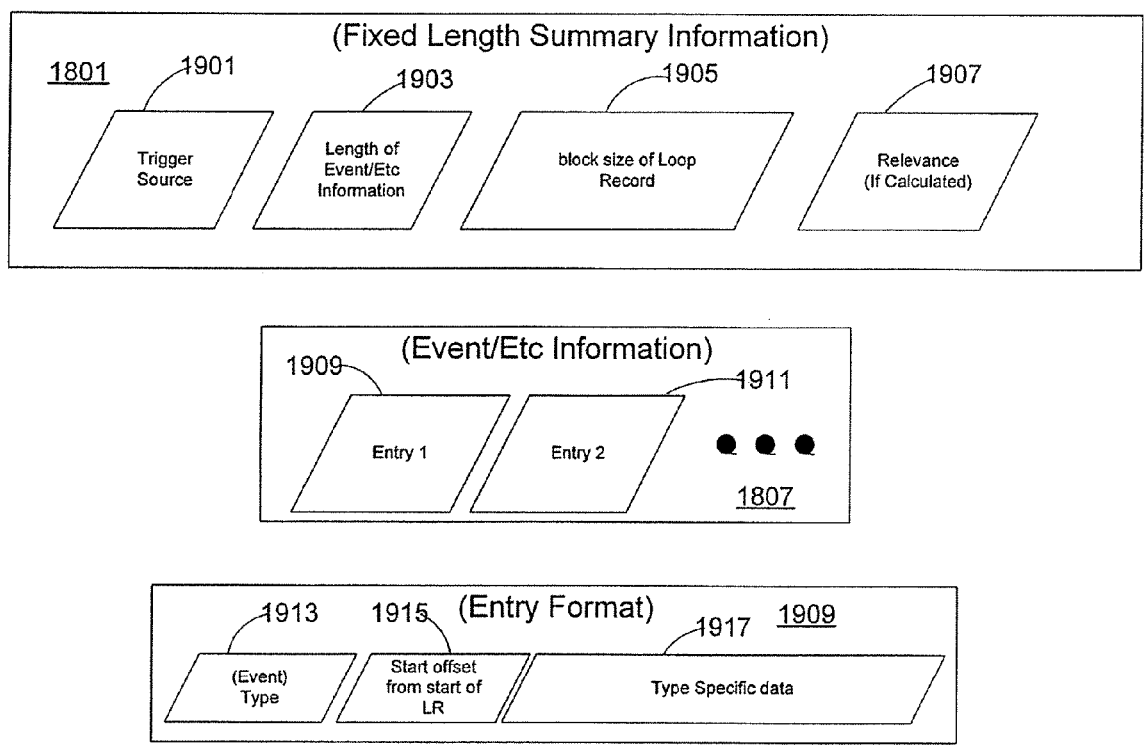
FIG. 19 shows components of the exemplary data entry as shown in FIG. 18.

FIG. 19 shows components of the exemplary physiological data as shown in FIG. 18. Summary information data 1801 includes trigger source data 1901, length of event/etc information data 1903, size of loop record 1905, and relevance information 1907. Trigger source data 1901 identifies what triggered recording (e.g., a neurological channel number). Length of event/etc information data 1903 is indicative of the length of event/etc data 1807, size of loop record 1905 contains the length of record 1800, and relevance data 1907 indicates the relevance level of each sampled channel as will be later discussed. Event/Etc information 1807 contains entries 1909 and 1911. Each entry includes event type 1913 that is indicative of an event associated with record 1800, start offset data 1915 includes the offset of record 1800 from the start of the loop recording, and type specific field 1917 includes specific data that is associated with the event. (However, in an embodiment of the invention, a data entry may store a pointer to physiologic data rather than store the physiologic data itself.) Record 1800 may be associated with a plurality of event types, each being indicated in separate entries, e.g., entries 1909 and 1911.

Data structure 1600 (as shown in FIG. 16) typically can store 1 to 16 Mbytes of data. Record 1800 may contain anywhere from approximately 5 Kbytes to approximately 1 Mbyte. Typically, a record contains 30-90 Kbytes per record. The embodiment supports both fixed size records (e.g. 60 Kbytes) or variable size records. With variable size records the retention scheme, as previously discussed, may require that a plurality of records or only portions of records be removed from circular buffer 201 in order to store a new record. Also, different parts of a record may be stored in physically different memory components (e.g., summary/header information data 601 in one place (a log) and sampled data 1803 and 1805 in another (waveform memory) with a pointer in the header/summary information indicating where the start of the data is and how much data is there).

As discussed, in an embodiment of the invention, a data record may be a pointer to physiologic data rather than store the physiologic data itself. Thus, for example, summary information data 1801 and/or event/etc information data 1807 may be stored in the first and second data structures wherein some or all of the entries may be mapped, via pointers, to more detailed and more space consuming waveform data (pre-detection data 1803, post-detection data 1805) in an associated memory (such as a loop record buffer).

Selective Storage of Data Channels

The embodiment supports the generation of records at different rates. The record rate will vary widely with an implanted device's configuration and with the patient. For example, a clinician may desire to record every detected seizure over a time period. There are some patients that have 1 seizure every 6 months, but there are some that have 500 seizures a day. A typical patient may have 2 unique events (seizure, button press, etc) per day.

While FIG. 18 shows an exemplary configuration with three neurological channels and an ECG channel, an embodiment of the invention supports a variable number of neurological channels so that the memory of an implanted device can store necessary information over a desired period of time. The channels may be adjusted either in quasi-static manner or in a dynamic manner. In an embodiment, the implanted medical device contains a channel selection component, which may be software or hardware logic for performing a process of selecting the one or more channels for data storage as described herein. An evaluation processing component may thereby obtain the selected channel data and process the channel data also in accordance with the techniques described herein.

For applications like the detection of epileptic seizures and the subsequent recording of data, it is advantageous, from a quality and resource stand-point, to be able to select a subset (which may include all physiologic channels) of the sensed input channels for detection processing and/or loop-recording. While this can be done manually prior to the availability of relevant data by defining the selected channels, manual configuration is less flexible and less desirable than allowing the closed-loop, real-time, quasi-real-time, periodic, or otherwise automated selection of physiologic channels.

With implantable detection algorithms and applications, there are typically a multitude of input sense channels. The degree of interest for each of these sense channels is often discernable while an implanted device is collecting data and storing the data in a memory component, e.g., a memory structure. As each sample is processed or stored as a short recording of samples, an application specific method may be employed to identify the most interesting (relevant) physiologic channels. Samples from selected physiologic channels may be utilized. Detection processing is typically resource intensive such that all physiologic channels may be utilized. Data recording in a loop-recording rapidly fills memory and then later prologs telemetry. In order to effectively process and store the samples, judicious selection of physiologic channels may be desired.

With a detection algorithm operating on physiological signals, it is likely that simply obtained information may reveal which channels to retain or continue processing. Often, physicians/users may be interested in examining, using, and retaining data from the physiologic channels in which an indication of an event is present. For example, if a seizure is detected on two of eight detection channels of data being recorded from the brain, only those two neurological channels need be retained. In this example, the savings in storage may be significant since only two channels are kept and six neurological channels are discarded, corresponding to a 4 to 1 sample compression.

Sample compression may be important if memory of an implanted device is limited. In the above example, one needs to decide which two channels should be kept. The decision may be based upon a number of factors including, independently-calculated channel severity (e.g., save the most severe), channel event onset time (e.g., save the first to detect), and seizure burden indication on the physiologic channel. In such a scenario, the flow diagram of FIG. 15 may be modified such that a severity calculation is performed prior to actual storage of the data in the first data structure. Or stored data records may be automatically removed from those data channels that are determined that the data is not important. Similarly, this approach may be extended to different and mixed physiologic signals. For example, if the multiple EEG channels are being polled, one may keep only those EEG channels where the neurological event data is most important (e.g., based on a severity scoring). If both cardiac, intra-cranial pressure (ICP) and EEG channels are being polled, one may keep only the signal types that deviated from norm. If the intra-cranial pressure rises significantly, one may keep samples from the ICP channel. If the previous scenario occurs while there is a tachycardia event, one may further keep samples from the ECG channel. Furthermore, if a seizure occurs near the same time, one may keep samples form all three channels.

The above approach may be extended to include the retention of more than one channel from a channel list sorted by relevancy as determined by a function of various factors (e.g., onset time, presence and severity of an event) as previously discussed. One may keep the most relevant physiologic channels of the channel list. For example, one may keep the three most relevant ("interesting") physiologic channels of five physiologic channels. Keeping the two or most relevant physiologic channels is referred as the "multi-max" of the channel list.

Alternatively, the system may retain a composite signal, which may be, for example, the sum of a plurality of channels. Other embodiments of the invention may utilize other derivatives. Furthermore, the channels themselves may be down-sampled or precision-reduced so that, for example, the least relevant samples are kept at 16 times less precision in amplitude and 2 times lower sampling rate resulting in about 4 times smaller data size.

Furthermore, with seizure detection and many other neurological applications the most interesting physiologic channels may be identified as those physiologic channels that are associated with the maximum energy value, normalized energy value, severity, or energy approximated value in the applications seizure frequency domain. For seizure detection, the seizure frequency domain may be 5-70 Hz (more narrowly this is typically 5-45 Hz) or (for fast ripple detections) at very high frequency (approximately 200 Hz or more). The energy value may often be sampled as the "rectified" (absolute value, square, etc.) of the samples taken directly from the filtered EEG signal. While this data may constantly be higher in some neurological locations, it is useful to normalize the data across the physiologic channels with manual or automatic gain control. Automatic gain control may be implemented as the daily comparison of running 1-pole filters and with the appropriate adjustment in response or in some other manner. For example, the gain of each physiologic channel may be adjusted so that the associated background signals are similar (to each other and/or to a target value), which may be referred to as background normalization. Because short signals may appear similar to interesting material over the short term, it is useful to smooth or reject outliers from the energy signals before comparison. Smoothing may be done, for example, using 1-pole filters, voting schemes, running or block percentile filters, percentile tracking technologies or slew-rate limiters to eliminate or mitigate, for example, the effect of epileptiform discharges (ED's) and sleep-spindles.

The embodiment supports different criteria for selecting channels for retention from a set of N physiologic channels. Different selection criteria include Max, MultiMax, MaxDeviationRetention, and Time-Distributed Max, MultiMax or MaxDeviation criterion. With the Max criterion, the physiologic channel with the highest energy is selected. With the MultiMax criterion, the M of N physiologic channels with the highest energy signals are selected. The selection may be implemented in a number of approaches, including multiple passes and sorting techniques. With the MaxDeviationRetention criterion, the physiologic channel with the highest energy is selected (as with the Max criterion). Moreover, P additional physiologic channels are selected that have an energy value greater than a determined fraction of the highest energy value. Variations of the above three criteria (Max, MultiMax, and MaxDeviation) may formed by selecting instantaneous values or by processing the physiologic channels with a window function. When determining a processed value, a physiologic channel maybe selected based on a configurable long to very short-term running window. The window may be based on any number of criteria including without limitation one or more of the following: median (or other percentile) of the window; mean of the window; running 1-pole value (e.g., one for each physiologic channel in which an associated time constant defines the width of an "effective" window); and accumulated absolute differences sum/accumulation (i.e., line-length). The accumulated difference criterion accumulates the difference of all channels with respect to a selected zero-channel. If there are accumulations greater than zero, the largest of those physiologic channels is selected.

With an embodiment of the invention, the selection of physiologic channels may occur after filtering (e.g., bandpass, notch, FIR, and IIR) the physiologic channels. For example, an EEG signal may be filtered in the 10-60 Hz range to remove the bulk of the EEG energy content that may otherwise mask the ictal content. As another example, the physiologic channels may be filtered in the 180-250 Hz range in order to study "fast-ripple" events.

The above channel selection process is applicable both for records stored in circular buffer 1601 and priority queue 1603. Moreover, the channel selection criterion for circular buffer 1601 may be different from the channel selection criterion for priority queue 1603.

In an embodiment of the invention, a "channel compositing" process is supported. A physiologic data sample is obtained from each of a subset of physiologic channels at an approximate time instance. For example, an implanted device may interface with N physiologic channels. A first subset of physiologic channels may include the first N/2 physiologic channels, a second subset may include the next N/2-1 physiologic channels, and a third subset may include the last physiologic channel. (A subset of physiologic channels may include all physiologic channels, one physiologic channel, or some number of physiologic channels in between.) Physiologic channels may be grouped into subsets in accordance different criterion, including the proximity of electrodes and the associated physiological functionality. A composite data may be determined from the sampled data of each subset of physiological data and stored in a data record. For example, the composite data may be the median value of the sampled data for the associated subset of physiologic channels. The embodiment may determine the composite data by other ways. For example, the minimum value, the maximum value, or the variation among the associated physiologic channels may be used. Also, the composite data may include a mixture of a plurality of physiologic data samples in a subset, e.g., a sum of selected physiologic data samples or a ratio of the largest physiologic data sample to the smallest physiologic data sample. Composite data is stored in a data record for each subset of physiologic channels.

Figure 20:
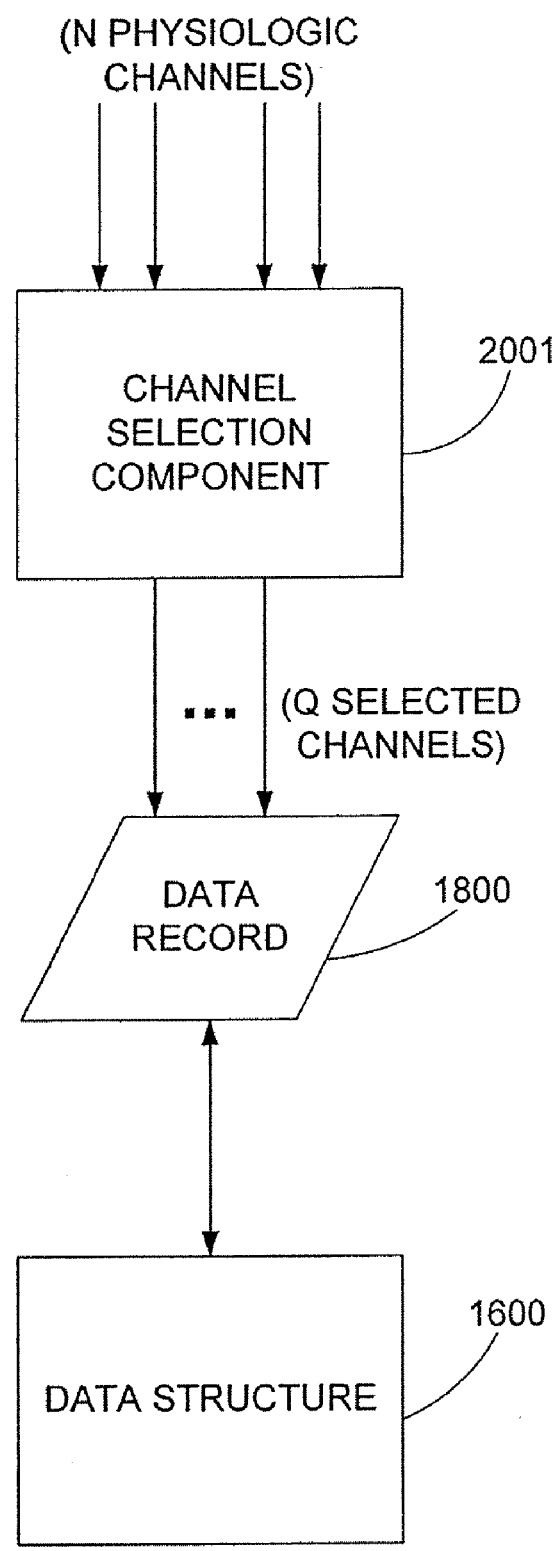
FIG. 20 shows the selection of channel data for retention in a data structure.

FIG. 20 shows the selection of channel data for retention in data structure 1600. In the embodiment, channel selection component 2001 and data structure 1600 are supported by an implanted component. Channel selection component 2001 obtains N physiologic channels from various sensors that may include neurological signals, EEG signals, and a mixture of physiologic signals. Channel selection component 2001 selects a subset of physiologic channels from the N physiologic channels using a selection criterion as previously discussed. Data from the selected physiologic channels is included in record 1800. Moreover, the selected physiologic channels may be processed by the implanted device and/or stored into memory. The embodiment, as shown in FIG. 20, stores record 1800 into data structure 1600 as previously discussed. Similarly, the above approach may be extended to different and mixed physiological signals.

In the embodiment, channel selection component 2001 includes a channel processor that selects a subset of physiological channels using the selection criterion. The channel processor may be implemented with a microprocessor, a signal processor, or other processor means.

Selective Storage of Peak Information

The system may also be configured to selectively store only portions of the data related to a seizure. For example, if peak information is desired, the system may be configured to store peak data information of a sensed signal. Thus, while a seizure might last several minutes, in an embodiment the space required to store the sensed signals associated with the seizure could be reduced by selecting portions of the sensed signal that were of more interest. As can be appreciated, this may be beneficial for implanted devices that have limited memory and power resources.

Figure 21:
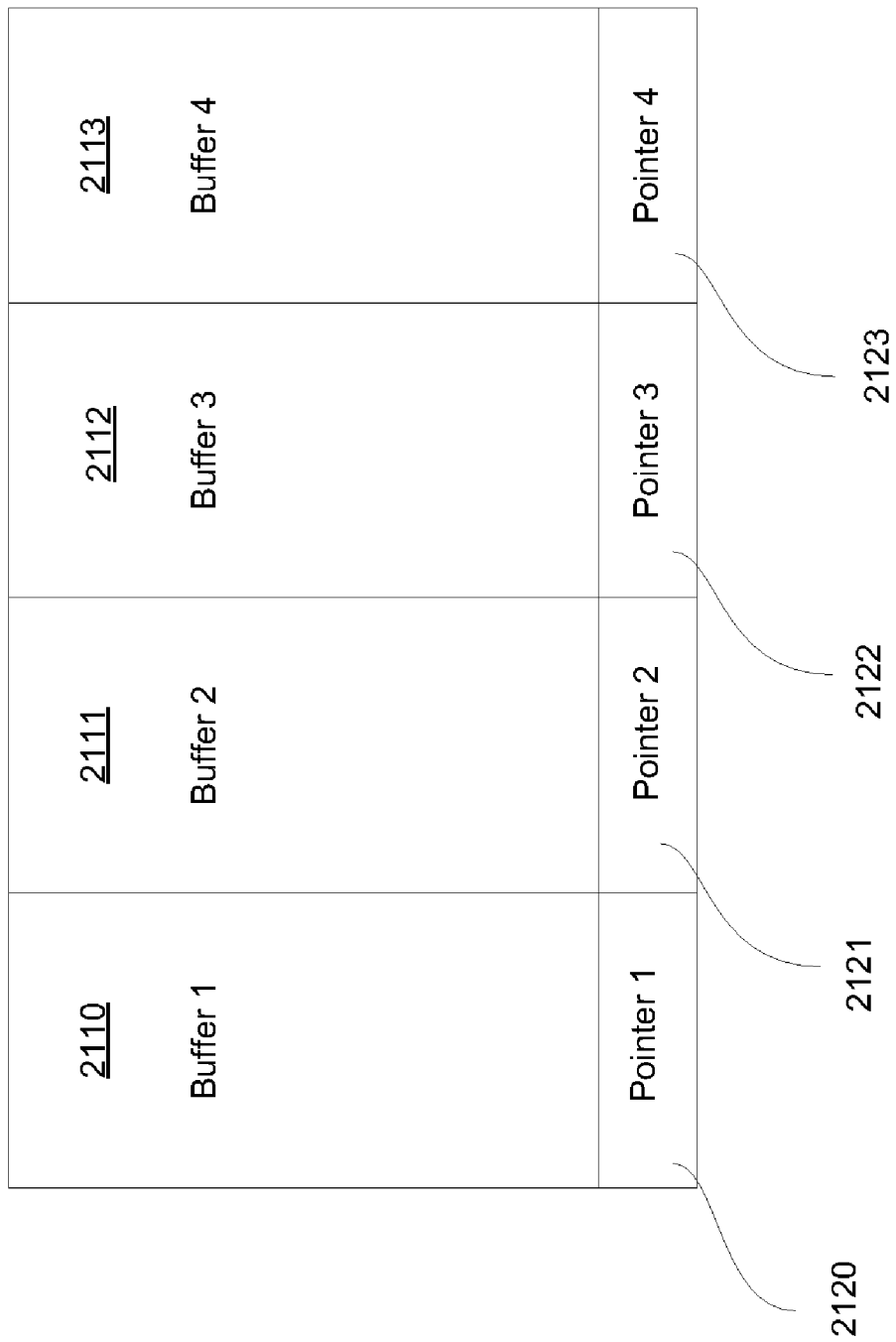
FIG. 21 shows an embodiment of a set of buffers.

FIG. 21 is a schematic of buffers 2110-2113 that may be used. As depicted four buffers are shown, however some other number of buffers may be used. In an embodiment, each buffer may store 20 seconds of signal data, however the size of the buffers used may vary. The amount of signal data that can be stored may also vary, depending on the encoding methods used to compress the stored data. The four buffers may be made of any type of known memory such as volatile or non-volatile RAM. As is known, volatile RAM tends to be faster and have a greater life expectancy but also tends to have greater power requirements. Thus, consideration of power and bandwidth requirements along with the expected life cycle of the produce can be expected to be among the factors that drive this design choice.

Figure 22:
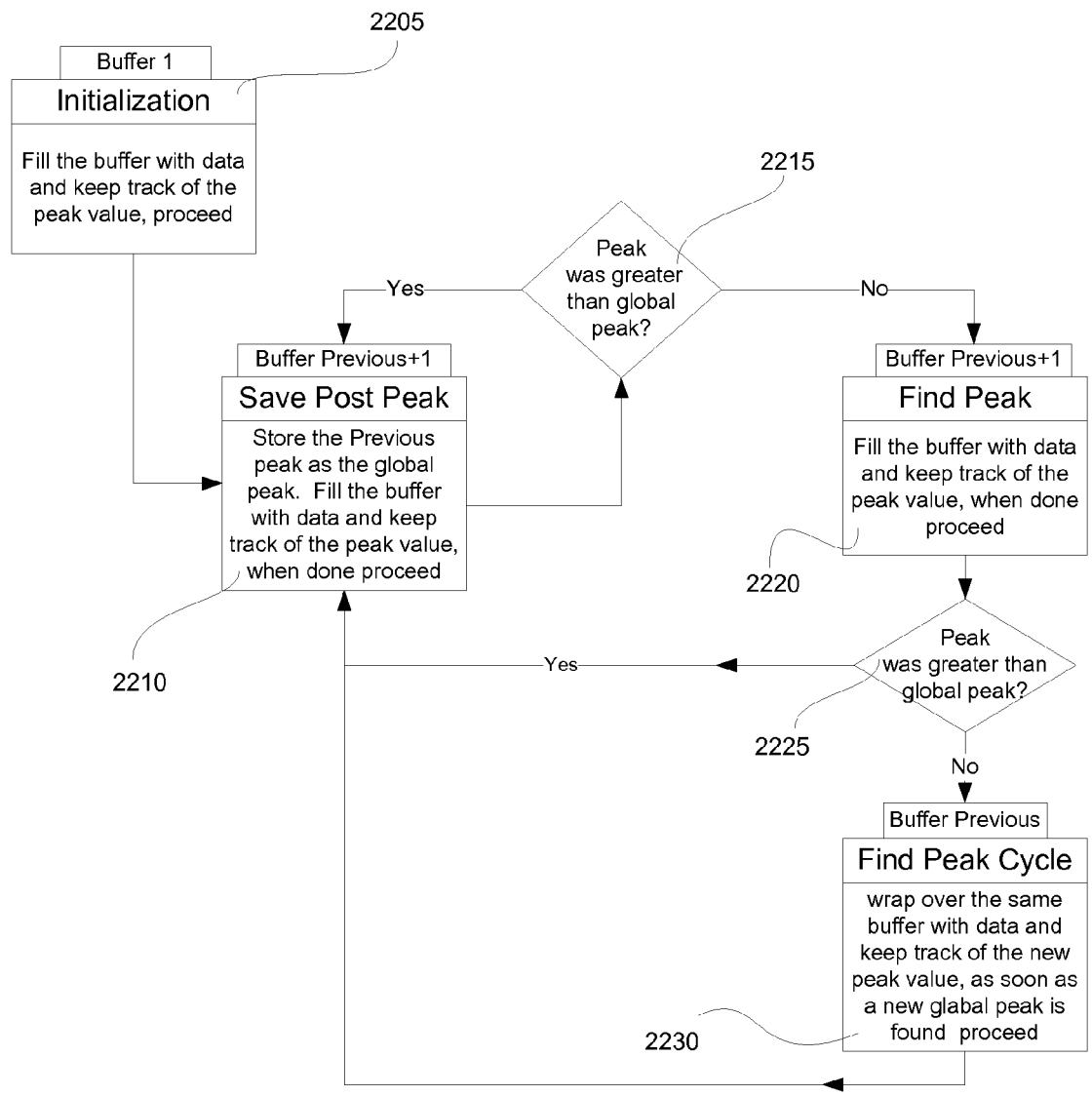
FIG. 22 shows an exemplary method of recording data in accordance with an embodiment of the invention.

FIG. 22 illustrates an example where data may be stored through use of the buffers depicted in FIG. 21. As depicted, the process starts at step 2205, labeled the Initialization box, where incoming signal data is stored in a first buffer. It should be noted that the initialization (e.g. the start of peak data recording) may occur in response to a detection of a seizure or in response to a trigger or an input, such as but not limited to, a manual trigger input provided by the patient.

The data to be stored in buffer may be one or more sensed signals (EEG, EKG, etc.) or it may be one or more measured signals that are derived from the sensed signals. In an embodiment, the measured signal to be stored in the buffer may be the severity rating of the sensed signal. The data, whether it is a digital version of the sensed signal or signals or whether it is derived from a sensed signal (or signals), will be referred to as signal data. As signal data is being stored in the first buffer, the system tracks the local peak value of the signal data in the first buffer with a first pointer 2120. Thus, the local peak value may be updated as the data is written into the buffer so there no need to go back and determine the local peak value for the buffer once the buffer is fully written. As can be appreciated, this is helpful when the buffer period is greater (such as 15-20 minutes or more) and searching for the peak value would be more computationally expensive.

The local peak value of the data stored in the first buffer is then used to update a global peak value (assuming that the global peak is reset with each initiation). While the global peak value may be updated after the first buffer is full, the global peak value may also be updated periodically (if there is a local peak value greater than the previous global peak value) or it may be updated substantially in real time as the local peak value is updated. While recording in the first buffer, however, it may be preferable to wait until the first buffer is full before updating the global peak value.

It should be noted that some other value in place of the peak value may be stored. For example, the minimum value may be stored or a peak change in value per time may be stored. One possible advantage of storing a minimum value is that certain individuals may experience a decrease in the amount of signal energy just prior to the onset of a seizure (what is sometimes referred to as electrodecremental of pre-ictal quieting effect), thus detecting and recording the relevant data may be of interest. Therefore, extreme data points may be monitored to determine whether the measured signal is of interest. For ease of discussion the following methods will refer to a peak value with the understanding that the peak value may be replaced with some other extreme value unless otherwise noted.

Next in step 2210, labeled the Save Post Peak box, the system continues to store the incoming signal data but in a second buffer 2111. As discussed above, the system tracks the local peak value of the stored data in the subsequent buffer with a pointer 2121.

Then in step 2215, the system compares the global peak value associated with pointer 2120 with the local peak value from the buffer 2111 that is associated with the pointer 2121. If the local peak value associated with pointer 2121 is greater than the global peak value (currently associated with pointer 2120), the global peak value is replaced with the local peak value from the buffer 2111. The process then loops back to step 2210 where the next set of incoming signal data is stored in a third buffer 2112 and the signal is stored as discussed above so that a local peak value may be associated with pointer 2122. Step 2215 is repeated and if the local peak value of buffer 2112 is greater than the global peak value (the global peak being associated with pointer 2121 in the current example), then the global peak is replaced with value associated with pointer 2122 and step 2210 is repeated again. As can be appreciated, this process continues with data next being stored in a fourth buffer 2113 and if the local peak continued to rise, the first buffer 2110 would then be over written. Thus, the four buffers 2110-2113 store signal data in a circular manner (e.g., with each buffer being overwritten every 4th period of time) so long as the local peak continued to rise.

While continuously rising local peak level values are possible, eventually, the local peak value can be expected to be less than the global peak value, possibly indicating a reduction in the severity of the seizure or perhaps indicating a temporary fluctuation in the measured signal values. Regardless of the reason, the determination in step 2215 will be that the local peak value is not greater than the global peak value and the process will proceed to step 2220, labeled the Find Peak box. In step 220, the signal data is stored in a subsequent buffer (buffer N) and a local peak value is determined. In step 2225, a check is made to see if the local peak value is greater than the global peak value. If it is, then step 2210 is repeated as discussed above. However, if the local peak value is again less than the global peak value, then step 2230 is next. In step 2230 the buffer is not incremented so the new signal data is stored in the previously used buffer. Additional data is overwritten in the buffer N in a circular manner (first in, first out or FIFO). Thus, if buffer N can hold 20 seconds of signal data, then after more than 20 seconds of recording the buffer N would have the most recent 20 seconds of data.

It should be noted that the buffer being overwritten in step 2230 is overwritten in a circular manner (FIFO) so that only the oldest information is being overwritten with each write of signal data. Therefore, if a local peak value is detected that is greater than the global peak value (the detection taking place substantially concurrently with the writing of the data), the writing of data in the buffer N is stopped and additional data is written in a subsequent buffer N+1 according to step 2210.

As can be appreciated, pointers may be used to indicate the start and stopping points. Furthermore, it may be useful to provide a pointer indicating the current location of storage in the buffer when the buffer is being used in a circular manner. In addition, the status of each buffer may be kept by tracking the state of the current and last three buffers and/or by keeping a Boolean for each buffer. The advantage of this system is that if the buffer is 20 seconds long, then the current buffer will contain data for the preceding 20 seconds less the last data point being written. The data in this buffer can be unwrapped during an analysis phase and will therefore provide almost 20 seconds of data prior to the global peak value (if the latest local peak value ends up being the global peak value). As can be appreciated, if a full 20 seconds of data preceding the peak value is desired, the buffer may be configured to hold 20 seconds plus one additional set of data.

As can be appreciated by the above discussion, the local peak value is continuously updated during step 2230 and is also continuously compared to the global peak value. Therefore, the local peak value of step 2230 may be considered an instantaneous peak value.

Thus, the process depicted in FIG. 22 is suited to store a buffer of data before, during and after the global peak. However, as the data in the buffer that is two periods after the global peak is of less interest, the data is not stored but is instead continuously overwritten until either a new global peak is detected or the measurement process ends. As noted above, the initiation of storing of signal data in a buffer may be triggered by any type of input desired, including detection of neurological events, detected elements of other physiological symptoms, device states (e.g., time outs) or the like. The end of storing may also be in response to a received input in a manner similar to the starting of the storing. The process in FIG. 22, however, merely controls which data is being stored in the buffers 2110-2113, which after the recording session ends may be archived in a second memory for further analysis.

Figure 24:
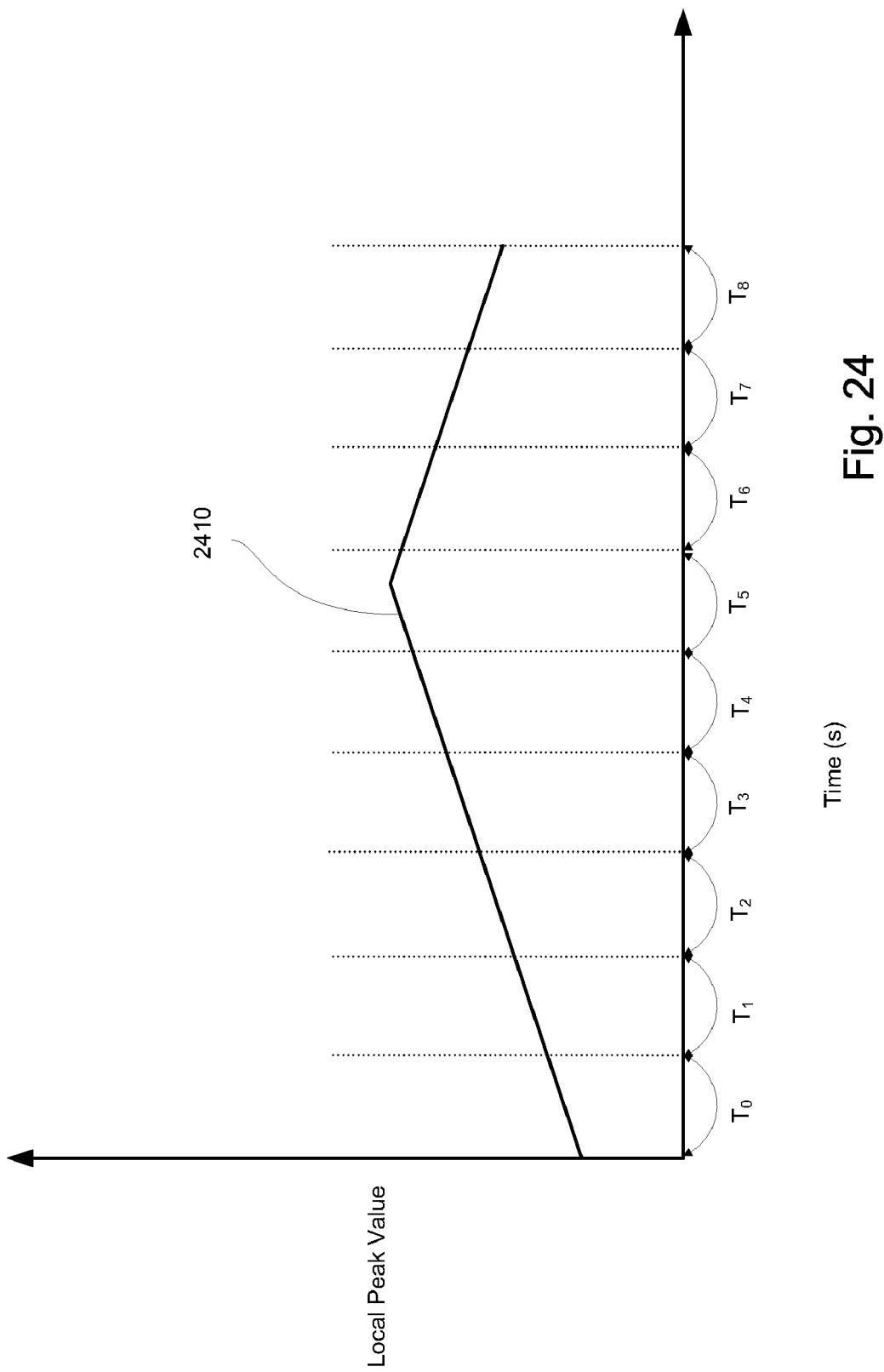
FIG. 24 shows an exemplary signal data line that may be recorded in accordance with an embodiment of the invention.

Look at FIGS. 21 and 24, an example is provided to further illustrate how the process depicted in FIG. 22 may work. It should be noted that the signal data line 2410 depicted in FIG. 24 is simplified for purposes of illustration. The signal data line 2410 represents the local peak value of each period T. It should be noted that in an embodiment the global peak value may be set to a theoretical minimum value, thus the first buffer will necessarily have a local peak value that exceeds the global peak value. Alternatively, the global peak value may be preset to some value that is considered a threshold value. In period $T_0$, the signal data is stored in buffer 2110 and the local peak value is determined to be greater than the global peak vale. Thus, the global peak value is set to the local peak value of buffer 2110. In period $T_1$, the signal data is stored in buffer 2111 and the local peak value is again greater than the global peak value so the global peak value is set equal to the local peak value in buffer 2111. Next the signal data in period $T_2$ is stored in buffer 2112 and the local peak value is determined to be greater than the global peak value. The global peak value is set equal to the local peak value of buffer 2112. The signal data from period $T_3$ is then stored in buffer 2113 and again the local peak value is determined to be greater than the global peak value so the global peak value is set equal to the local peak value of buffer 2113. Next the signal data from period $T_4$ is stored in buffer 2110, overwriting the previous data, and again the local peak value is determined to be greater than the global peak value so the global peak value is set equal to the updated local peak value of buffer 2110. Next the signal data from period $T_5$ is stored in buffer 2111, overwriting the previous data, and a new local peak value is determined to be greater than the global peak value so the global peak value is set to the new local peak value of buffer 2111. Next the signal data from period $T_6$ is stored in buffer 2112, overwriting the previous data, and this time the local peak value is determined to be less than the global peak value, therefore the global peak value is not changed. Next the signal data from period $T_7$ is stored in buffer 2113, overwriting the previously stored signal data, and the local peak value is again determined to be less than the global peak value. As this is the second period in a row with a local peak value less than the global peak, the next period $T_8$ is stored in buffer 2113, overwriting the data that was just stored in the previous period. The recording session ends after period $T_8$.

In the embodiment depicted, buffer 2110 includes signal data from the period before the global peak value, buffer 2111 includes signal data from the period that includes the global peak value, and buffer 2112 includes signal data from the period after the global peak value. This data may be archived in a second memory so as to preserve it for later analysis. The data in buffer 2113, however, may be ignored or saved as it represents the final period of data before the end of the recording session.

Thus, as illustrated, the method depicted in FIG. 22 allows for a convenient way to collect the most interesting data surrounding an extreme data point (the global peak value) while minimizing the need for a large buffer sufficient to hold the entire recording period.

As can be appreciated, it is possible that the first period recorded has the local peak value that turns out to be the global peak value. In such a scenario, there would be less data prior to the occurrence of the global peak. However, as this data was not otherwise available, the disclosed methods provide satisfactory results with the data that is available. As can be appreciated, a comparable situation exists for the last period recorded in which there would be less data following the occurrence of the global Peak.

It should be noted that while a local peak value of the current buffer being used to record the signal data can be determined to be greater than the global peak in somewhat real time, determining whether the local peak value of the current buffer will actually be the global peak value for the entire recording session requires knowledge of additional signal data. A full determination requires knowledge about all the data up until the conclusion of recording session, however, if a period of time such as a subsequent buffer does not have a local peak value greater than the local peak value of the current buffer, an initial determination can be made that the local peak value of the subsequent buffer is not the global peak value (and the current local peak value can be treated as the global peak value).

As can be appreciated, to conserve power, it is preferable that signal data stop being stored in the buffers at some point (until the next event triggers the recording process). In addition, the signal data adjacent the triggering of the storing of signal data may become of less interest as it becomes more remote from the triggering event. Therefore, it is expected that in one embodiment the data recording will begin and end (thus providing a recording session) and that the period captured will contain the local peak value that ends up being the global peak value.

If the global peak value is near the end of the recording session, it may be that less data will be available after the global peak value. However, as noted above, it is expected that almost a full buffer of signal data preceding the global peak value will be stored and signal data after the global peak will also be stored in a subsequent buffer to the extent there is additional time left to record the signal data before the recording session ends.

Figure 23:
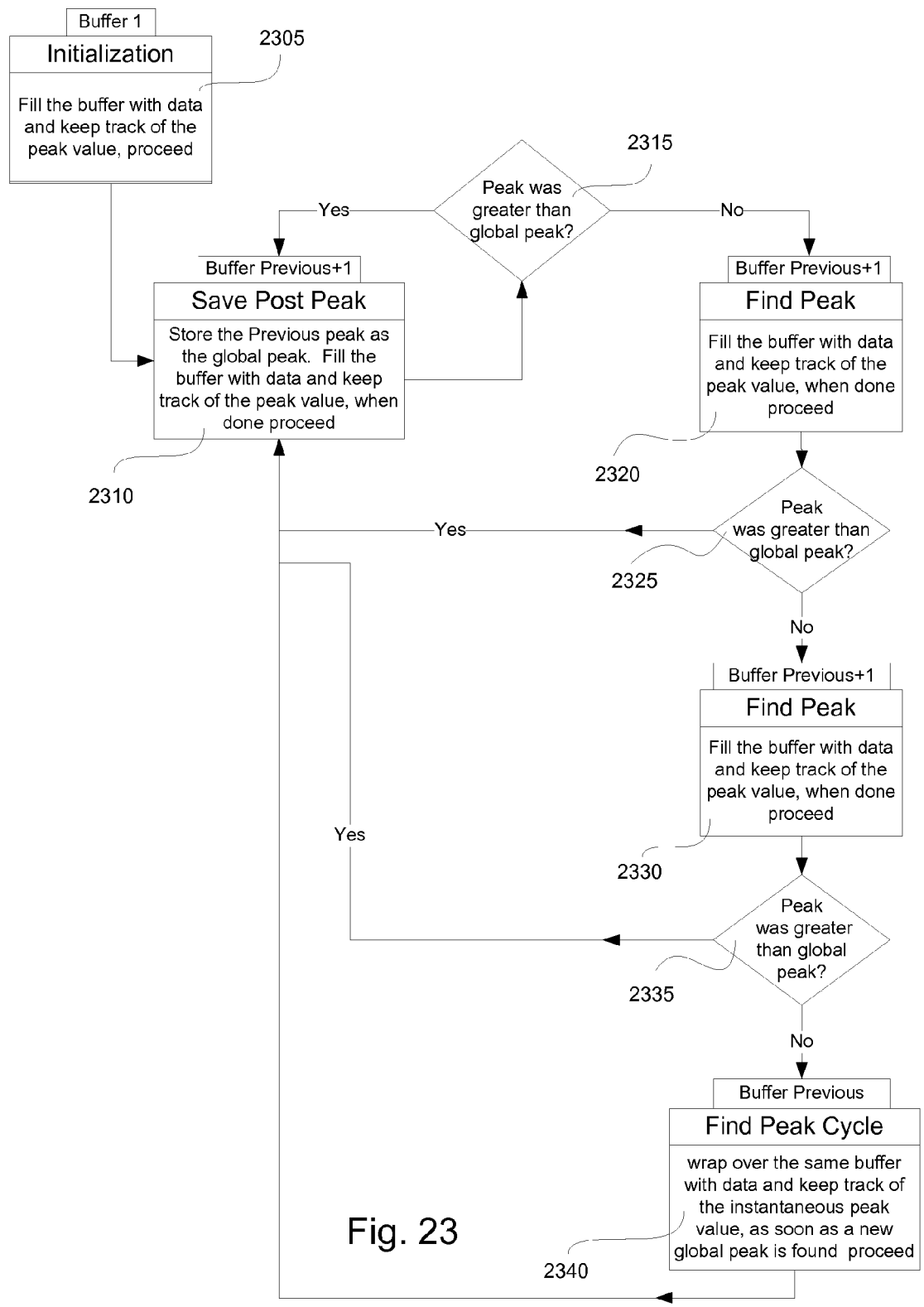
FIG. 23 shows an alternative exemplary method of recording data in accordance with an embodiment of the invention.

FIG. 23 illustrate an alternative process for storing signal data. As can be appreciated, steps 2305 through steps 2325 are similar to steps 2205 through steps 2225 and for the sake of brevity the entire above discussion will not be repeated. In step 2330, however, the signal measurements are stored in a subsequent buffer N+1 rather than the same buffer N as in step 2230 and another check is made to see if the local peak value is greater than the global peak value in step 2335. If it is not, in step 2340 the signal measurement data is recorded in buffer N+1, overwriting the data that was stored in step 2330. The signal data continues to be overwritten into the buffer N+1 in a circular manner (FIFO) until either the local peak value exceeds the global peak value or the recording period ends. As discussed above with respect to step 2130, if a new global peak value is detected, no further data is written in the buffer N+1 and step 2310 is done. As before, in step 2310 the buffer is incremented and signal data is stored in the subsequent buffer.

Looking again at the data signal embodiment depicted in FIG. 24, the process depicted in FIG. 23 would provide that at the end of the period $T_8$, the signal data from $T_5$ would be stored in buffer 2111, the signal data from $T_6$ would be stored in buffer 2112, the signal data from $T_7$ would be stored in buffer 2113 and the signal data from $T_8$ would be stored in buffer 2110, thus overwriting the signal data from $T_4$.

Thus, FIG. 23 illustrates a method that may provide two buffer periods of signal data after a buffer is noted is determined to have a local peak value greater than the global peak value. In a four buffer system, this has the effect of shifting the saved signal data from before, during and after a global peak value (such as can be expected to be provided by the method in FIG. 22) to during and after the global peak value with more signal data after the global peak being saved. As can be appreciated, an alternative method may shift the data so as to provide more information before the global peak value. Therefore, the signal data stored in the three buffers may be considered a window that is adjustable so as to allow for a focused storage of what is determined to be the most desired data. The determination of where to set the window can depend on whether pre or post global peak data is determined to be more important or if the data before and after the global peak is considered equally important.

It should be noted that additional buffers may be added to increase the amount of data stored before and after what is determined to be the global peak value. However, this may increase cost and power consumption. It is also possible to use less than four buffers; however this would either require saving less data or a more complex process may be required that uses more computation power.

FIGS. 25 and 26a-26f illustrate an embodiment of a more complex data storage method. A buffer 2605 is provided. As depicted, buffer 2605 is a single physical buffer that is three times as large as a buffer period 2607 of data (e.g., S to M1, M1 to M2, and M2 to E) that is desired before a global peak; however, in an alternative embodiment three separate buffers, each the size of the buffer period 2607, could also be used. Thus, the buffer 2605 is an example of a buffer set. A buffer set may have one or more physically distinct buffers that are the size of the buffer period 2607 or that it may be dividable into buffer periods 2607. Thus, the buffer period 2607 may refer to a physically distinct buffer or a portion of the buffer and the buffer portion may or may not be physically continuous.

Figure 26A:
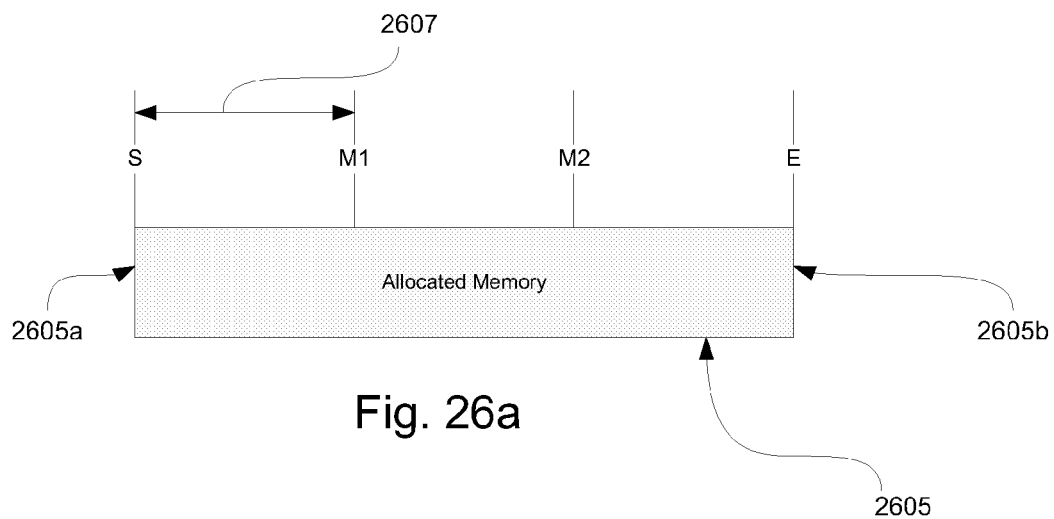
FIGS. 26a-26f show embodiments of signal data stored in a buffer in accordance with an embodiment of the invention.
Figure 26B:
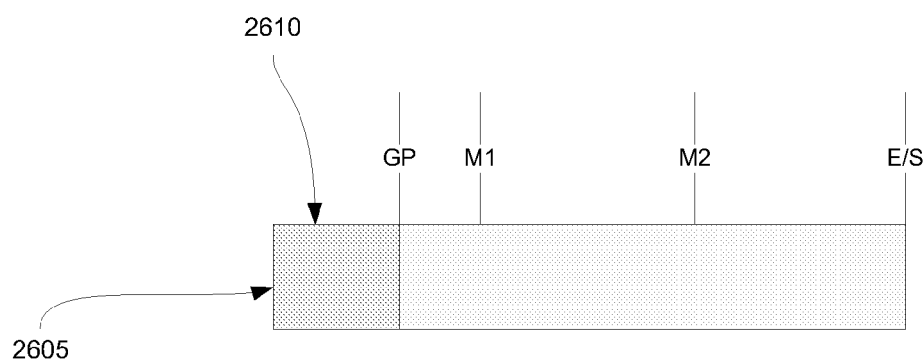

The initialization of data storing starts with step 2510 where signal data is stored in a buffer 2605. Next in step 2515, a check is made to determine whether the recently stored data is the global peak. If not, in step 2520 a check is made to see whether the period since the recording of the global peak has reached the end of the after global peak period. It should be noted that if there is no threshold value for the global peak, the first value will be a global peak and each successful value that exceeds the current global peak will also be a global peak. Alternatively, if there is a threshold level for the global peak, then an initial period 2610, before the first global peak, may wrap around the buffer 2605 one or more times and may even continuous wrap around until the end of the recording period. However, the more likely occurrence is that after a period of time, a current value of the signal data will exceed the initial global peak (or the global peak threshold, if used). Thus, referring to FIG. 26*b*, after the initial period 2610, the global peak is detected. As can be appreciated, FIG. 26*b* represents an embodiment using the global peak threshold because otherwise the initial period 2610 before the first global peak would not exist.

Referring again to FIG. 25, the detection of the global peak causes the answer in step 2515 to be yes. Next in step 2530, the location of the pointers is adjusted. In FIG. 26*c*, the pre-global peak period ("pre-GPP") is less than the buffer period 2607; however as the depicted method did not start recording prior to initial point, this cannot be helped. Thus, as depicted, when the global peak is detected less than the buffer period 2607 from the beginning of the recording session, the amount of signal data prior to the determined global peak will be less than desired. It is expected that the more regular occurrence will be a situation where the global peak occurs after more than a buffer period 2607 of signal data is stored. In such a case, the point where the global peak is detected will be set to be M2 (as in FIG. 26*c*) but unlike FIG. 26*c*, the portion 2615 will include a full buffer period 2607 of signal data and therefore there will not be any unused portion 2640.

After the pointers are adjusted, data is stored in a subsequent position in the buffer in step 2510. As depicted, each time data is stored the checks in steps 2515 and 2520 are made. If no additional global peak is detected, the answer to step 2520 will eventually be yes. When that happens, the end of the post-global peak period ("post-GPP") is marked in step 2535. This indicates that the amount of signal data stored after the global peak is equal to the buffer period 2607. Depending on when the current global peak took place, the pre-GPP may or may not be as large as the buffer period 2607.

Next in step 2540, signal data is stored in a subsequent portion of the buffer 2605. It should be noted that if an end 2605*b* of the buffer 2605 is reached, this may involve wrapping around to a beginning 2605*a* of the buffer 2605. As depicted, with each storage of signal data, a check is made to see if the signal data being stored exceeded the global peak in step 2545 or if the buffer period 2607 of signal data has been stored in step 2550. If the answer to both is no, then step 2540 is repeated. It should be noted that step 2540 may direct the signal data to be stored in front of the buffer 2605 Eventually, however, if the answer to step 2545 remains no, the answer to step 2550 will be yes and then the location in the buffer 2605 where the next portion of signal data will be stored will reset in step 2655 to correspond to the location that is just after the end of the location that was used to store the portion of the signal data in the post-GPP. Then in step 2540, the location of data storage will be incremented and the signal data will overwrite the previously stored signal data in portion 2630. Thus, looking at FIG. 26*c*, the portion 2630 of the buffer 2605 will be used to store signal data in a circular manner (FIFO), with the newest signal data overwriting the older signal data until ether the answer to 2545 is yes or the data recording session ends.

It should be noted that there is an unused portion 2640. This is because, as discussed above, less than a full buffer period 2607 of data was stored before the last global peak was detected. To simplify the method of data storage, this portion of the buffer 2605 may be ignored in such a circumstance. However, the amount of signal data being saved after the global peak could be increased by this amount in a case where less than a full buffer period 2607 of signal data was stored before the first global peak was detected. Alternatively, the portion of the buffer 2605 that was being used in a circular manner could also be increased.

Figure 26C:
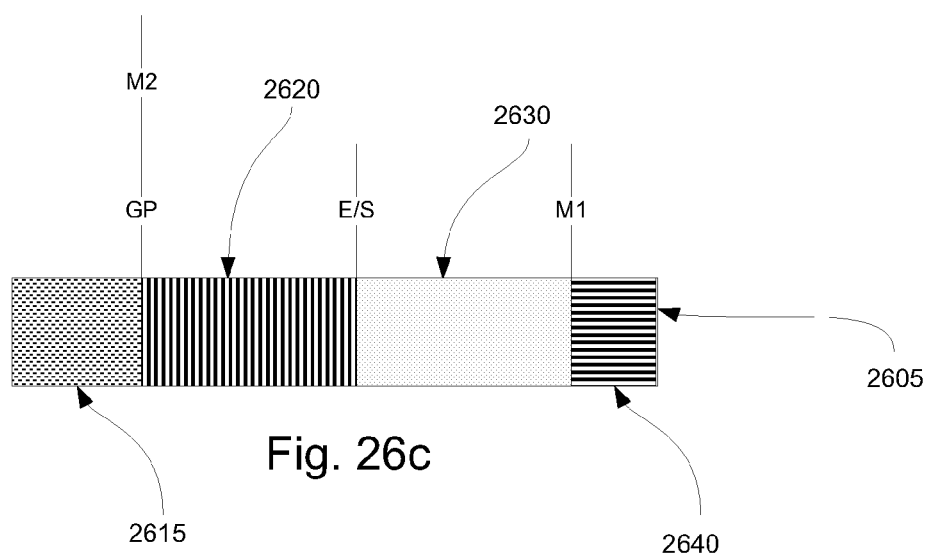
Figure 26D:
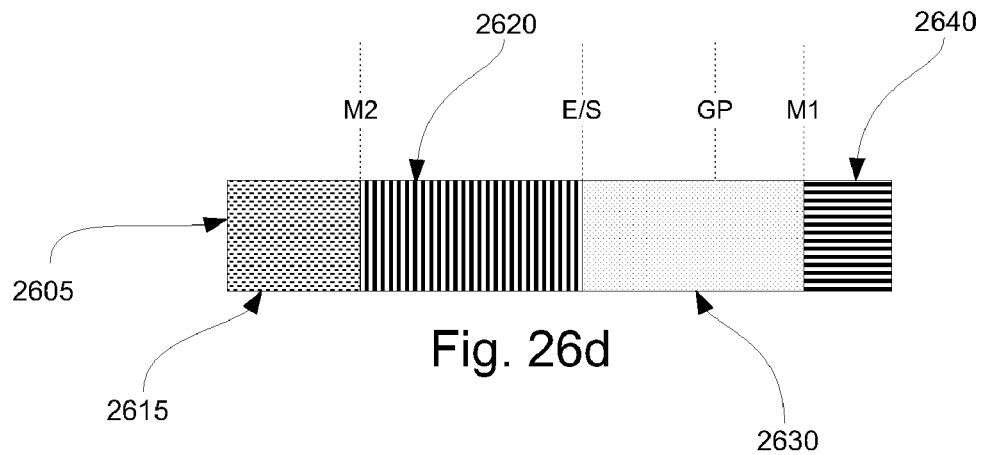
Figure 26E:
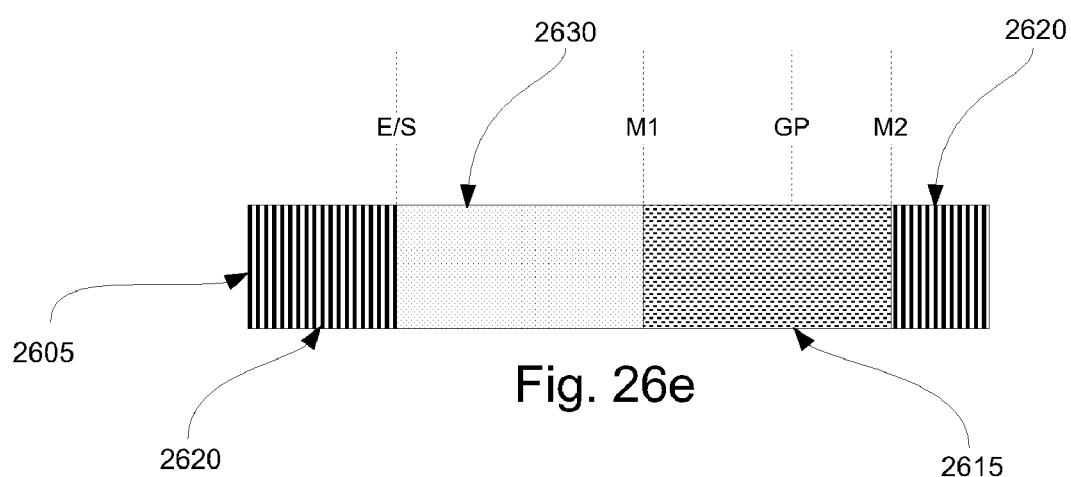

It is expected that a case with a later detected global peak is probable. Thus, the answer to step 2545 is expected to be yes at some point. When this occurs, such as depicted in FIG. 26*d*, recording is stopped in the portion 2630, the pointers are reset in step 2530 and the signal data is stored in what was previously unused portion 2640. As can be appreciated, the pre-GPP period 2615 now includes the global peak in a portion of the buffer that 2605 that is out of order. Signal data is stored in portion of the buffer 2605 extending between M2 and E/S of FIG. 26*e*. Once the answer to 2520 is yes, then steps 2535-2555 are repeated as discussed above.

Figure 26F:
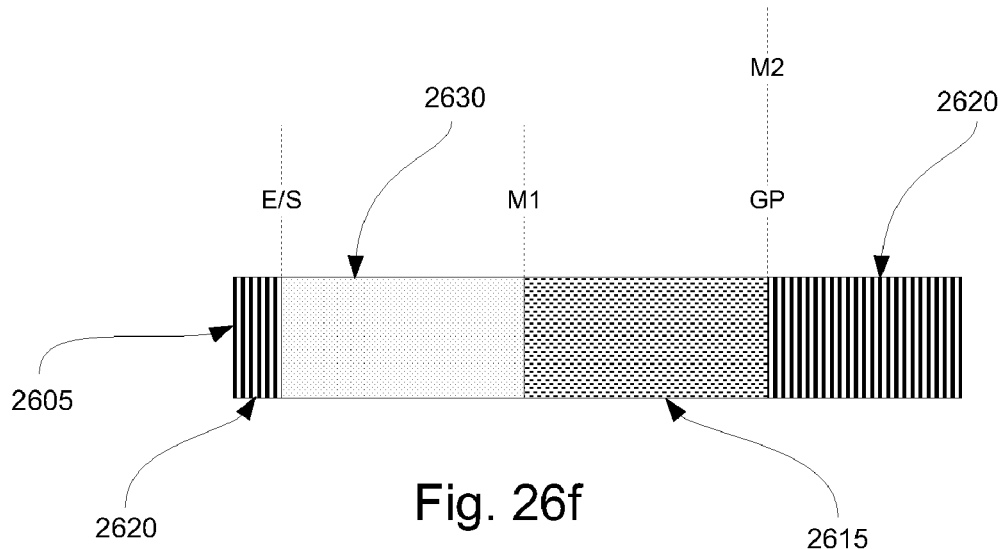

It should be noted that step 2530 may include additional functionality. For example, the signal data stored in period 2615 could be unwrapped so that all data that was stored before the global peak (the pre-GPP) is located in the portion of the buffer 2605 that precedes the global peak. Similarly, the data stored in the post-GPP period can be moved so that its direction follows the global peak. Thus, the signal data may be stored in the buffer 2605 in a manner as disclosed in FIG. 26*f*. In an embodiment, the shifting can take place in response to the detection of the new global peak as part of step 2530. As before, once the buffer period 2607 of signal data after the global peak is stored (portion 2620 in FIGS. 26*c*-26*f*), the next buffer period 2607 is used to store signal data in a circular manner (e.g., FIFO). As can be appreciated, unwrapping or shifting the data can be useful for cases where an initially determined global peak value in the portion 2630 (which is likely to be out of order) is quickly followed by another local peak value that ends up being the global peak value. In such a situation, having the data out of order may be problematic and require more complicated tracking of when each piece of data was stored. Therefore, shifting the position of the data in response to a detection of a new global peak can avoid this issue. In an embodiment, the shifting may take place all at once in response to the detection of the new global peak. Thus, looking at FIGS. 26*d*-26*f*, upon the detection of the global peak in portion 2630, the portion 2615 of FIG. 26*f* could be immediately formed and subsequent data would be written until portion 2620 was as shown in FIG. 26*f*. In an alternative embodiment, the shifting may move the prior signal data just prior to the writing of new signal data.

Figure 25:
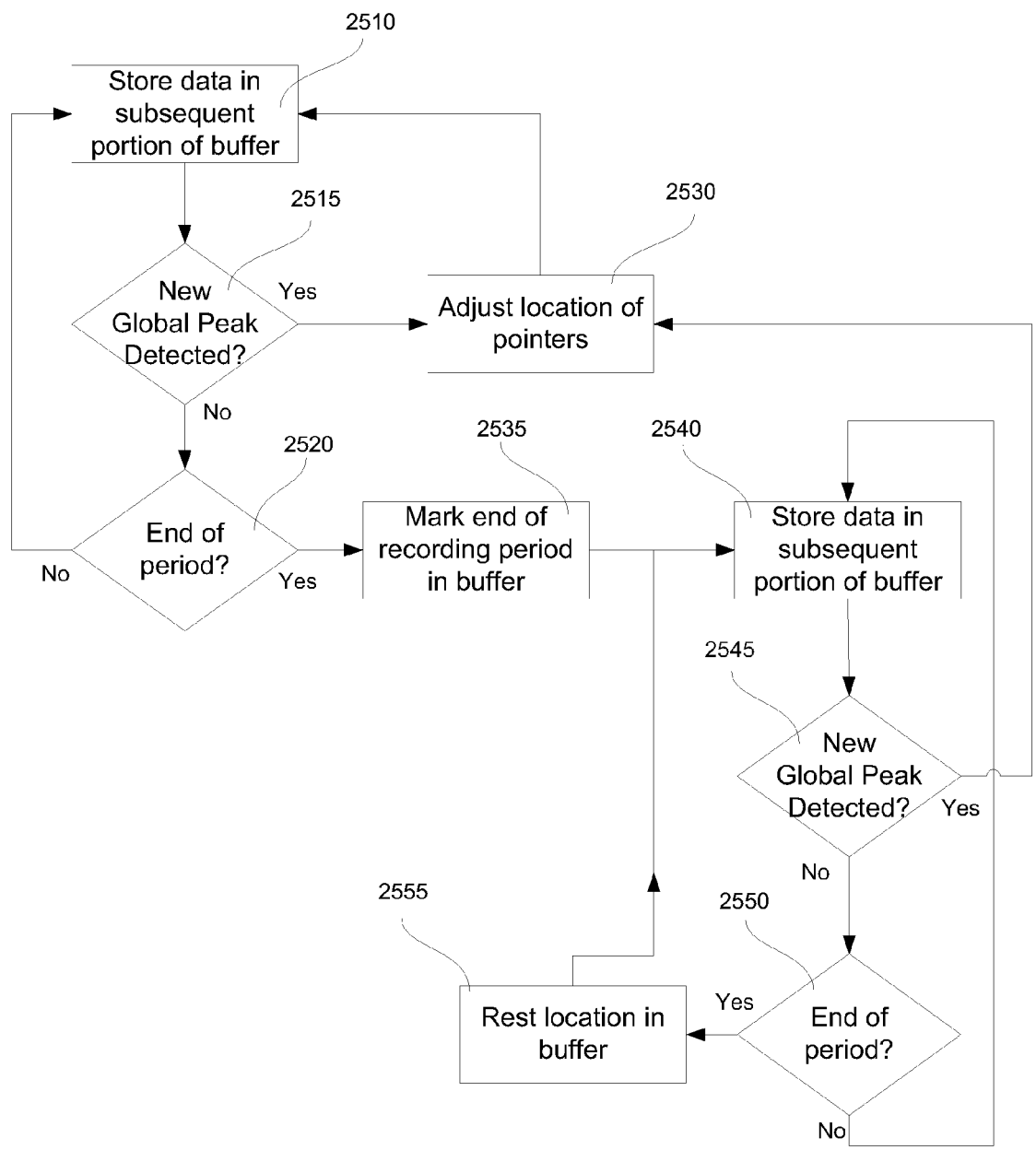
FIG. 25 shows an alternative exemplary method of recording data in accordance with an embodiment of the invention.

Thus, the method depicted in FIGS. 25-26*f* illustrates a more complex version of data storage method described in FIG. 22. Comparatively speaking, the method in FIG. 25 uses less overall memory to preserve the desired portion of signal data while using a more complex method of handling the storage of the signal data. Other variations are also possible. As can be appreciated, the decision of whether to use a more complex method that requires less memory or to use a simpler method that requires more memory is a system level trade-off that may be made based on available processing resources and reserve energy (e.g., battery power) provided by the implanted device as well as other considerations such as the cost and type of the memory used.

As can be appreciated by one skilled in the art, a computer system with an associated computer-readable medium containing instructions for controlling the computer system can be utilized to implement the exemplary embodiments that are disclosed herein. The computer system may include at least one processor such as, but not limited to, a microprocessor or a digital signal processor, and associated peripheral electronic circuitry. In an embodiment, all or a portion of the instructions may be hardwired into digital logic blocks and the computer system can be designed as an embedded system so as to potentially conserve energy while potentially loosing a certain degree of flexibility. Numerous other variations in using a processor (i.e. a logic machine) to carry out logic instructions are possible.

Thus, embodiments of the invention are disclosed. One skilled in the art will appreciate that the above teachings can be practiced with embodiments other than those disclosed. The disclosed embodiments are presented for purposes of illustration and not limitation, and the inventions are limited only by the claims that follow.

What is claimed is:

1. A method of selectively storing signal data in an implantable device, comprising:
   (a) in response to initiation of a recording period, storing signal data in a buffer of an implantable device in a circular manner, the buffer being configured to store at least three buffer periods of data, the storing including a determination of a new local value each time signal data is stored;
   (b) automatically setting a global extreme value equal to the new local value when the new local value exceeds the global extreme value;
   (c) storing signal data in the buffer in a first buffer period following the determination of a new global extreme value and repeating step (b) if a local value associated with signal data stored in the buffer during the first buffer period is determined to exceed the global extreme value;
   (d) storing signal data in the buffer in a circular manner for a second buffer period and repeating step (b) if a subsequent signal data being stored in the second buffer period is determined to exceed the global extreme value; and
   (e) storing at least a portion of the signal data in the buffer in a memory if the signal data in the buffer is determined to be of interest.

2. The method of claim 1, wherein the storing in (e) is based on whether the signal data in the buffer is determined to exceed a priority of data already stored in the memory.

3. The method of claim 1, wherein the at least a portion of signal data includes about a buffer period of signal data immediately preceding the signal data associated with the global extreme value and about a buffer period of signal data immediately following the signal data associated with the global extreme value.

4. The method of claim 1, wherein the storing in the memory takes place after the recording period ends.

5. The method of claim 1, wherein the buffer is volatile RAM and the memory is non-volatile RAM.

6. The method of claim 1, wherein the global extreme value must exceed a predetermined minimum value.

7. A method of selectively storing signal data in an implantable device, comprising:
   (a) storing signal data in a buffer of an implantable device in a circular manner during a recording period, the buffer configured to contain at least three buffer periods of data;
   (b) preserving about a buffer period of signal data before and after a determined global extreme value;
   (c) continuing to store an additional buffer period of signal data in the buffer in a circular manner once the signal data is preserved, the additional buffer period of signal data being overwritten by subsequent signal data unless a new global extreme value is determined;
   (d) if the new global extreme value is determined in (c), repeating step (b); and
   (e) if the stored signal data is determined to be of interest, storing at least a portion of the preserved signal data in a memory.

8. The method of claim 7, wherein the signal data is stored after the recording period ends.

9. The method of claim 7, wherein the global extreme value exceeds a predetermined minimum value.

10. The method of claim 7, wherein the global extreme value does not need to exceed a predetermined minimum value.

11. The method of claim 7, wherein a value associated with each subsequent signal data stored in (a) is compared to the global extreme value, wherein the global extreme value is automatically updated when the value of the subsequent signal data exceeds the global extreme value.

12. A method of selectively storing signal data in an implantable device, comprising:
   (a) storing signal data in a buffer of an implantable device in a circular manner during a recording period, the buffer configured to store at least three buffer periods of signal data, wherein a new local value is determined each time new signal data is stored;
   (b) automatically causing a global extreme value to equal the new local value when the new local value exceeds the global extreme value; and
   (c) preserving in the buffer about a first buffer period of signal data before the global extreme value and preserving in the buffer about a second buffer period after the global extreme value, while continuing to store a third buffer period of subsequent signal data, wherein the signal data being stored in the third buffer period is overwritten in a circular manner when the signal data exceeds what can be stored in the third buffer period; and
   (d) storing the signal data preserved in the buffer in a memory if the preserved signal data is determined to be of interest.

13. The method of claim 12, wherein the buffer can hold about three buffer periods of signal data.

14. The method of claim 13, wherein the buffer holds three buffer periods of signal data and one additional set of signal data associated with a single value.

15. The method of claim 12, wherein the automatically causing the global extreme value to equal the new local value further comprises adjusting a pointer so that the pointer points to the signal data associated with the global extreme value.

16. The method of claim 12, wherein the determining that the signal data is of interest is based on the value of the global extreme value compared to global extreme values associated with signal data previously stored in the memory.

17. The method of claim 12, further comprising:
   (e) repeating step (b) when the new local value occurring during the preserving of signal data in the second buffer period exceeds the global extreme value.

* * * * *